(12) United States Patent
Mansfield et al.

(10) Patent No.: US 7,723,364 B2
(45) Date of Patent: *May 25, 2010

(54) N-[2-(2-PYRIDINYL) ETHYL]BENZAMIDE COMPOUNDS AND THEIR USE AS FUNGICIDES

(75) Inventors: Darren James Mansfield, Lyons (FR); Pierre-Yves Coqueron, Lyons (FR); Philippe Desbordes, Lyons (FR); Heiko Rieck, Sainte-Foy-les-Lyon (FR); Marie-Claire Grosjean-Cournoyer, Curis Au Mont d'OR (FR); Pierre Genix, Lyons (FR); Alain Villier, Saint Cyr Au Mont d'OR (FR); Isabelle Christian, Lyons (FR)

(73) Assignee: Bayer Cropscience SA (FR)

( * ) Notice: Subject to any disclaimer, the term of this patent is extended or adjusted under 35 U.S.C. 154(b) by 999 days.

This patent is subject to a terminal disclaimer.

(21) Appl. No.: 10/566,051

(22) PCT Filed: Jul. 19, 2004

(86) PCT No.: PCT/EP2004/009145

§ 371 (c)(1),
(2), (4) Date: Apr. 18, 2006

(87) PCT Pub. No.: WO2005/014545

PCT Pub. Date: Feb. 17, 2005

(65) Prior Publication Data

US 2006/0246102 A1  Nov. 2, 2006

(30) Foreign Application Priority Data

Jul. 25, 2003  (EP) .................... 03356116

(51) Int. Cl.
*A01N 43/40* (2006.01)
*C07D 213/61* (2006.01)
*C07D 213/40* (2006.01)

(52) U.S. Cl. .......... 514/357; 514/344; 514/345; 514/348; 514/349; 514/350; 514/351; 514/352; 514/354; 514/356; 546/330; 546/335; 546/337

(58) Field of Classification Search ........... 546/330, 546/335, 337; 514/344, 345, 348, 349, 350, 514/351, 352, 354, 356, 357

See application file for complete search history.

(56) References Cited

U.S. PATENT DOCUMENTS

| 3,995,044 A | 11/1976 | Kabbe et al. |
| 4,006,239 A | 2/1977 | Mayer et al. |
| 6,821,992 B1 * | 11/2004 | Cooke et al. ............ 514/336 |

FOREIGN PATENT DOCUMENTS

| EP | 0 284 174 | 9/1988 |
| EP | 1 389 614 | 2/2004 |
| WO | WO 99/42447 | 8/1999 |
| WO | WO 01/11965 | 2/2001 |
| WO | 2004016088 | * 2/2004 |

* cited by examiner

*Primary Examiner*—Patricia L Morris
(74) *Attorney, Agent, or Firm*—Ostrolenk Faber LLP

(57) ABSTRACT

Compound of general formula (I):

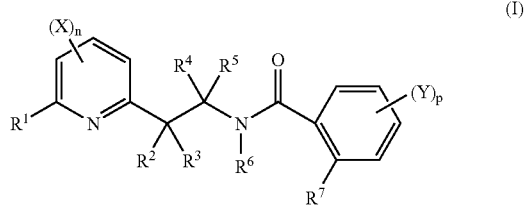

Process for preparing this compound.

Fungicidal composition comprising a compound of general formula (I).

Method for treating plants by applying a compound of general formula (I) or a composition comprising it.

15 Claims, No Drawings

N-[2-(2-PYRIDINYL) ETHYL]BENZAMIDE COMPOUNDS AND THEIR USE AS FUNGICIDES

CROSS-REFERENCE TO RELATED APPLICATION(S)

The present application is a 35 U.S.C. §371 national phase conversion of PCT/EP2004/009145, filed Jul. 19, 2004, which claims priority of European Application No. 03356116.8 filed Jul. 25, 2003.

The present invention relates to novel N-[2-(2-pyridinyl) ethyl]benzamide derivatives, their process of preparation, their use as fungicides, particularly in the form of fungicidal compositions, and methods for the control of phytopathogenic fungi of plants using these compounds or their compositions.

The international patent application WO 01/11965 discloses a broad family of fungicidal compounds in which the 2-pyridyl group is substituted by at least one halogenoalkyl group.

It is always of high-interest in agriculture to use novel pesticidal compounds in order to avoid or to fight the development of resistant strains to the active ingredients used by the farmer. It is also of high-interest to use novel compounds being more active than those already known, with the aim of decreasing the amounts of active material to be used by the farmer, whilst at the same time maintaining an effectiveness at least equivalent to the already known compounds.

We have now found a new family of compounds which possess the above mentioned characteristics.

Accordingly, the present invention relates to N-[2-(2-pyridinyl)ethyl]benzamide derivative of general formula (I):

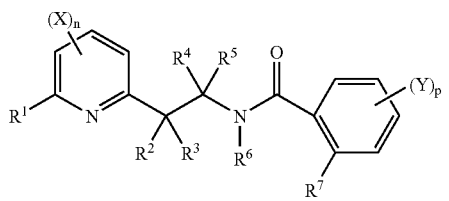

(I)

in which:

n is 1, 2 or 3;

X is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;

$R^1$ is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl optionally substituted with 1 to 5 halogen atoms, a benzylamino, a phenoxy, a phenylsulfanyl optionally substituted with 1 to 5 halogen atoms or a phenylamino;

with the proviso that X and $R^1$ are not both a hydrogen atom;

$R^2$ and $R^3$ are the same or different and are a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonyloxy or a $C_1$-$C_6$-alkylcarbonylamino;

or $R^2$ and $R^3$ may together form a 3-, 4-, 5- or 6-membered carbocycle;

$R^4$ and $R^5$ are the same or different and are a hydrogen atom, a halogen atom, a cyano group, a $C_1$-$C_6$-alkyl or a $C_1$-$C_6$-halogenoalkyl having 1 to 5 halogen atoms;

or $R^4$ and $R^5$ may together form a 3-, 4-, 5- or 6-membered carbocycle;

$R^6$ is a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-cycloalkyl, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalkylsulfonyl having 1 to 5 halogen atoms;

p is 1, 2, 3 or 4;

Y is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide; and $R^7$ is a halogen atom, a nitro group, a cyano group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;

as well as its salts, N-oxides, metallic and metalloidic complexes.

In the context of the present invention:

halogen means fluorine, bromine, chlorine or iodine.

carboxy means —C(=O)OH; carbonyl means —C(=O)—; carbamoyl means —C(=O)NH$_2$; N-hydroxycarbamoyl means —C(=O)NHOH;

an alkyl group, an alkenyl group, and an alkynyl group as well as moieties containing these terms, can be linear or branched.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

Any of the compound of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compound of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compound of general formula (I) wherein $R_1$ represents a hydroxy or sulfanyl group, and/or X represents a hydroxy, sulfanyl or amino group, may be found in its tautomeric form resulting of the shift of the proton of said hydroxy, sulfanyl or amino group. Such tautomeric forms of such compounds are also part of the present invention. More generally speaking, all tautomeric forms of compounds of general formula (I) wherein $R_1$ represents a hydroxy or sulfanyl group, and/or X represents a hydroxy, sulfanyl or amino group, as well as the tautomeric forms of the compounds which can optionally be used as intermediates in the preparation processes, and which will be defined in the description of these processes, are also part of the present invention.

According to the present invention, the 2-pyridyl is substituted in 6-position by $R^1$ and may be substituted in any other position by $(X)_n$, in which X and n are as defined above. Preferably, the present invention relates to N-[2-(2-pyridinyl) ethyl]benzamide derivative of general formula (I) in which the different characteristics may be chosen alone or in combination as being:

as regards $R^1$, $R^1$ is a hydrogen atom or a halogen atom;

as regards n, n is 1 or 2;

as regards X, X is a halogen atom or a $C_1$-$C_8$-alkyl;

as regards the positions in which the 2-pyridyl moiety is substituted by X, the 2-pyridyl moiety is substituted by X in 3- and/or in 5-position.

According to the present invention, the phenyl is substituted in ortho position by $R^7$ and may be substituted in any other position by $(Y)_p$, in which Y and p are as defined above. Preferably, the present invention relates to N-[2-(2-pyridinyl) ethyl]benzamide derivative of general formula (I) in which the different characteristics may be chosen alone or in combination as being:

as regards $R^7$, $R^7$ is a halogen atom, a $C_1$-$C_8$-alkyl or a $C_1$-$C_8$-halogenoalkyl having 1 to 5 halogen atoms;

as regards p, p is 1 or 2. More preferably, p is 1.

as regards Y, Y is a hydrogen atom, a halogen atom or a $C_1$-$C_8$-alkyl. More preferably Y is a hydrogen atom;

as regards the positions in which the phenyl moiety is substituted by Y, the phenyl moiety is substituted by Y preferentially first in para position.

The present invention also relates to a process for the preparation of the compound of general formula (I). Thus, according to a further aspect of the present invention there is provided a process (A) for the preparation of compound of general formula (Ia)

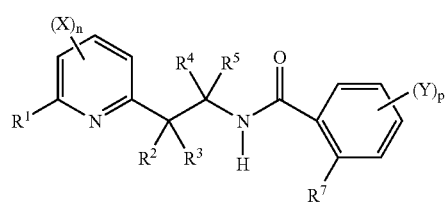

(Ia)

wherein: $R^1$, $R^2$, $R^7$, X, Y, n and p are as defined above;
$R^3$ is a $C_1$-$C_6$ alkyl;

which comprises
a first step according to reaction scheme A-1:

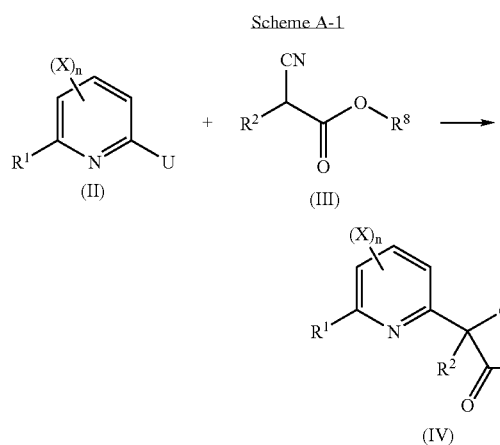

Scheme A-1 in which:
$R^1$, $R^2$, X and n are as defined above;
$R^8$ is a $C_1$-$C_6$ alkyl, a $C_1$-$C_6$ haloalkyl, a benzyl, 4-methoxybenzyl or pentafluorophenyl;
U is a leaving group chosen as being a halogen, a $C_1$-$C_6$ alkylsulfonate or a $C_1$-$C_6$ haloalkylsulfonate;

comprising the arylation of a cyanoacetate derivative of general formula (III) by a pyridine derivative of general formula (II), to provide a 2-(pyridyl)cyanoacetate derivative of general formula (IV), in the presence of a base, at a temperature of from 0° C. to 200° C.;
a second step according to reaction scheme A-2:

Scheme A-2

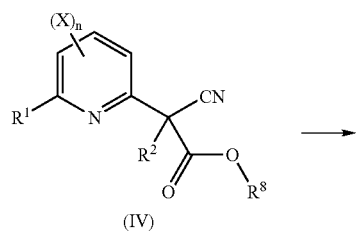

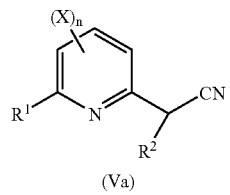

(Va)

in which:
$R^1$, $R^2$, X, n are as defined above;
$R^3$ is a hydrogen atom;
$R^8$ is a $C_1$-$C_6$ alkyl, a $C_1$-$C_6$ haloalkyl, a benzyl, 4-methoxybenzyl or pentafluorophenyl;

comprising a basic hydrolysis, an acidic hydrolysis or a displacement by an halide of a compound of general formula (IV) in the same or a different pot to provide, upon heating at a temperature of from 40° C. to reflux, a 2-pyridylacetonitrile derivative of general formula (Va);
a third step according to reaction scheme A-3:

Scheme A-3

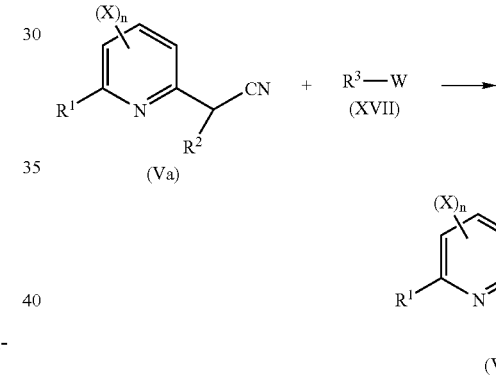

in which:
$R^1$, $R^2$, X, n are as defined above;
$R^3$ is a $C_1$-$C_6$ alkyl;
W is a halogen atom, a $C_1$-$C_6$ alkylsulfonate, a $C_1$-$C_6$ haloalkylsulfonate or a 4-methyl-phenylsulfonate, comprising the alkylation of a compound of general formula (Va) by a reagent of general formula (XVII) to provide a compound of general formula (Vb);
a fourth step according to reaction scheme A-4:

Scheme A-4

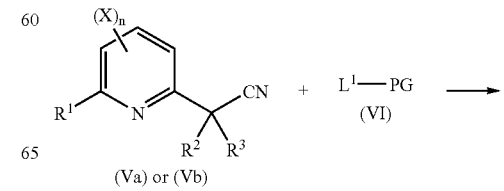

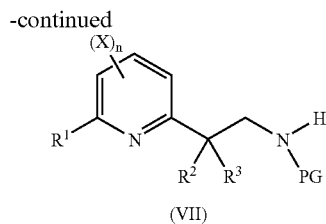

(VII)

in which:

R$^1$, R$^2$, X, n are as defined above;

R$^3$ is a hydrogen atom or a C$_1$-C$_6$ alkyl;

L$^1$ is a leaving group chosen as being a —OR$^8$ group or a —OCOR$^8$ group, R$^8$ being a C$_1$-C$_6$ alkyl, a C$_1$-C$_6$ haloalkyl, a benzyl, 4-methoxybenzyl or pentafluorophenyl;

PG represents a protecting group which may be a —COOR$^8$ group or —COR$^8$ group; R$^8$ being a C$_1$-C$_6$ alkyl, a C$_1$-C$_6$ haloalkyl, a benzyl, 4-methoxybenzyl or pentafluorophenyl;

comprising the reduction, by hydrogenation or by an hydride donor, of a compound of general formula (Va) or (Vb), in the presence of a catalyst and in the presence of a compound of general formula (VI) to produce a compound of general formula (VII), at a temperature of from 0° C. to 150° C. and under a pressure of from 1 bar and 100 bar;

a fifth step according to reaction scheme A-5:

Scheme A-5

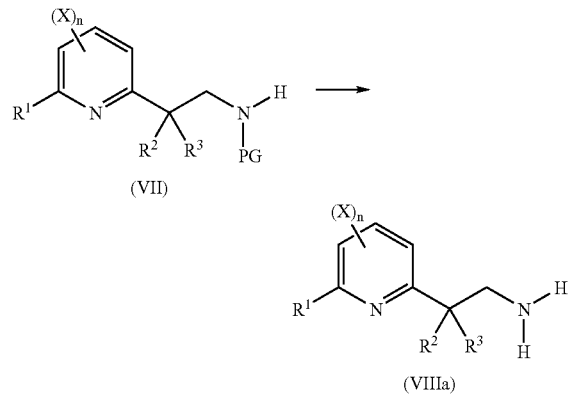

(VII)

(VIIIa)

in which:

R$^1$, R$^2$, X, n are as defined above;

R$^3$ is a C$_1$-C$_6$ alkyl;

PG represents a protecting group which may be a —COOR$^8$ group or —COR$^8$ group, R$^8$ being a C$_1$-C$_6$ alkyl, a C$_1$-C$_6$ haloalkyl, a benzyl, 4-methoxybenzyl or pentafluorophenyl;

comprising a deprotection reaction, in an acidic or in a basic medium, of a compound of general formula (VII) to provide an amine derivative of general formula (VIIIa) or one of its salt;

a sixth step according to reaction scheme A-6:

Scheme A-6

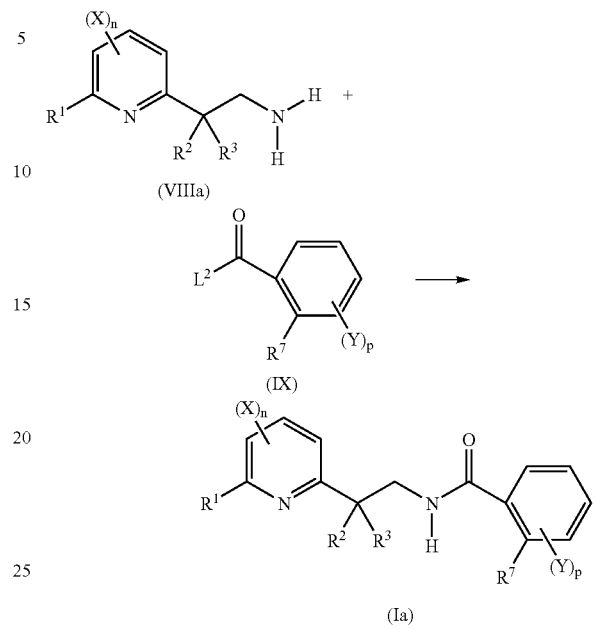

(VIIIa)

(IX)

(Ia)

in which:

R$^1$, R$^2$, R$^7$, X, Y, n and p are as defined above;

R$^3$ is a C$_1$-C$_6$ alkyl;

L$^2$ is a leaving group chosen as being a halogen atom, a hydroxyl group, an OR$^8$ group, an OCOR$^8$, R$^8$ being a C$_1$-C$_6$ alkyl, a C$_1$-C$_6$ haloalkyl, a benzyl, 4-methoxybenzyl or pentafluorophenyl; or a group of formula

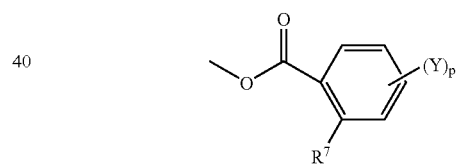

comprising a coupling reaction of an amine derivative of general formula (VIIIa) or one of its salt, with a carboxylic acid derivative of formula (IX) to provide a compound of general formula (Ia).

The first step (step A-1) of the process A according to the present invention is conducted in the presence of a base. Preferably, the base will be chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The first step (step A-1) of the process A according to the present invention is conducted at a temperature of from 0° C. to 200° C. Preferably, first step (step A-1) is conducted at a temperature of from 0° C. to 120° C., more preferably at a temperature of from 0° C. to 80° C.

The first step (step A-1) of the process A according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step A-1) of the process A according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(–)-1-[(S)-2-(dicyclohexylphosphino)ferrocenyl]ethyldicyclohexylphosphine and its corresponding enantiomer, or a mixture of both; (R)-(–)-1[(S)-2-(dicyclohexylphosphino)ferrocenyl]hyldiphenylphosphine and its corresponding enantiomer, or a mixture of both; (R)-(–)-1[(S)-2-(diphenylphosphino)ferrocenyl]ethyldi-t-butylphosphine and its corresponding enantiomer, or a mixture of both; or (R)-(–)-1[(S)-2-(diphenylphosphino)ferrocenyl]ethyldicyclohexylphosphine and its corresponding enantiomer, or a mixture of both.

The fourth step (step A-4) of the process A according to the present invention is conducted in the presence of a hydride donor. Preferably, the hydride donor is chosen as being metal or metalloid hydrides such as $LiAlH_4$, $NaBH_4$, $KBH_4$, $B_2H_6$.

The fourth step (step A-4) of the process A according to the present invention is conducted in the presence of a catalyst. Preferably, the catalyst is chosen as being Co(II)-Chloride, Ni(II)-chloride, ammonia or one of its salt, Palladium on charcoal, Raney Nickel, Raney Cobalt or Platinum.

The fourth step (step A-4) of the process A according to the present invention is conducted at a temperature of from 0° C. to 150° C. Preferably the temperature is of from 10° C. to 120° C. More preferably, the temperature is of from 10° C. to 80° C.

The fourth step (step A-4) of the process A according to the present invention is conducted under a pressure of from 1 bar to 100 bar. Preferably the pressure is of from 1 bar to 50 bar.

The fourth step (step A-4) of the process A according to the present invention may be conducted in the presence of an organic solvent, of water or of a mixture thereof. Preferably, the solvent is chosen as being ether, alcohol, carboxylic acid, or a mixture thereof with water or pure water.

The present invention also relates to another process for the preparation of the compound of general formula (I). Thus, according to a further aspect of the present invention there is provided a second process B for the preparation compound of general formula (Ia)

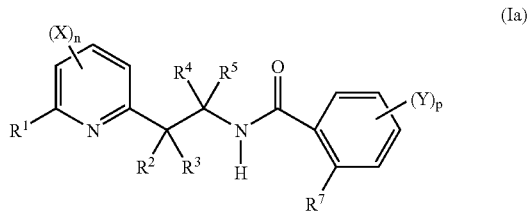

(Ia)

wherein: $R^1$, $R^2$, $R^7$, X, Y, n and p are as defined above; $R^3$ is a $C_1$-$C_6$ alkyl;

which comprises
a first step according to reaction scheme B-1:

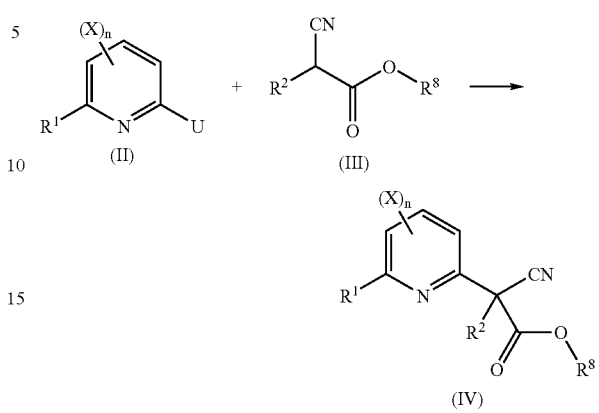

Scheme B-1 in which: $R^1$, $R^2$, X and n are as defined above;
$R^8$ is a $C_1$-$C_6$ alkyl, a $C_1$-$C_6$ haloalkyl, a benzyl, 4-methoxybenzyl or pentafluorophenyl;
U is a leaving group chosen as being a halogen atom, a $C_1$-$C_6$ alkylsulfonate or a $C_1$-$C_6$ haloalkylsulfonate;

comprising the arylation of a cyanoacetate derivative of general formula (III) by a pyridine derivative of general formula (II) to provide a 2-pyridylcyanoacetate derivative of general formula (IV);

a second step according to reaction scheme B-2:

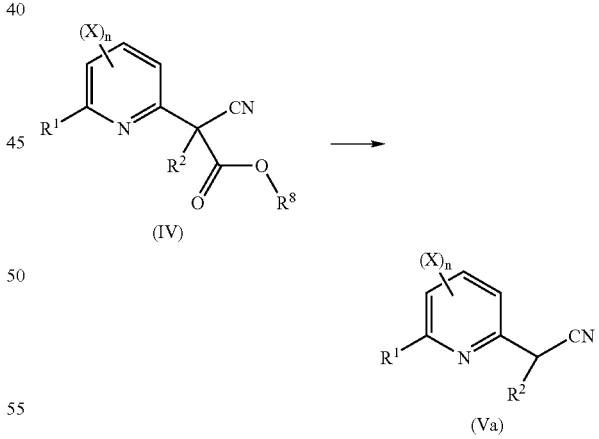

Scheme B-2 in which: $R^1$, $R^2$, X and n are as defined above;
$R^8$ is a $C_1$-$C_6$ alkyl, a $C_1$-$C_6$ haloalkyl, a benzyl, 4-methoxybenzyl or pentafluorophenyl;

comprising a basic hydrolysis, an acidic hydrolysis or a displacement by an halide of a compound of general formula (IV) in the same or a different pot to provide, upon heating at a temperature of from 40° C. to reflux, a 2-pyridylacetonitrile derivative of general formula (Va);

a third step according to reaction scheme B-3:

Scheme B-3

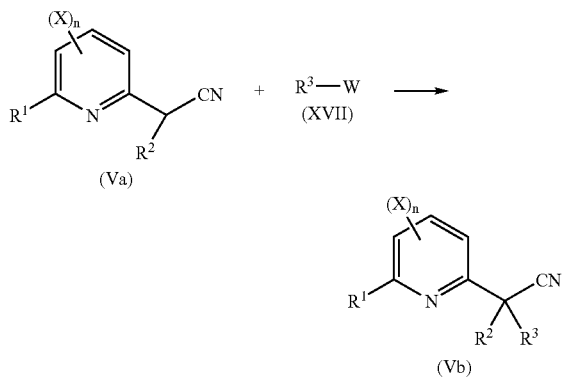

in which:
R$^1$, R$^2$, X, n are as defined above;
R$^3$ is a C$_1$-C$_6$ alkyl;
W is a halogen atom, a C$_1$-C$_6$ alkylsulfonate, a C$_1$-C$_6$ haloalkylsulfonate or a 4-methyl-phenylsulfonate, comprising the alkylation of a compound of general formula (Va) by a reagent of general formula (XVII) to provide a compound of general formula (Vb);

a fourth step according to reaction scheme B-4:

Scheme B-4

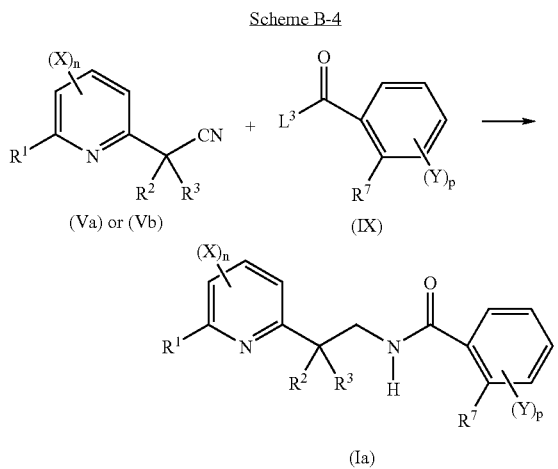

in which:
R$^1$, R$^2$, R$^7$, X, Y, n and p are as defined above;
R$^3$ is a C$_1$-C$_6$ alkyl;
L$^3$ is a leaving group chosen as being —OCOR$^8$, R$^8$ being a C$_1$-C$_6$ alkyl, a C$_1$-C$_6$ haloalkyl, a benzyl, 4-methoxybenzyl or pentafluorophenyl; —OCHO, —SCSN(Me)$_2$ or a group of formula comprising the reduction by hydrogenation or by an hydride of a compound of general formula (Va) or a compound of general formula (Vb) in the presence of a catalyst and in the presence of a compound of general formula (IX) to produce a compound of general formula (Ia), at a temperature of from 0° C. to 150° C. and under a pressure of from 1 bar and 100 bar.

Compound of general formula (Ia) according to the present invention may be prepared according to the process B.

The preferred conditions under which step B-1 of the process B is conducted are the same than the preferred conditions under which step A-1 of the above mentioned process A is conducted.

The preferred conditions under which step B-2 of the process B is conducted are the same than the preferred conditions under which step A-2 of the above mentioned process A is conducted.

The preferred conditions under which step B-3 of the process B is conducted are the same than the preferred conditions under which step A-3 of the above mentioned process A is conducted.

The preferred conditions under which step B-4 of the process B is conducted are the same than the preferred conditions under which step A-4 of the above mentioned process A is conducted.

The present invention also relates to another process for the preparation of the compound of general formula (I). Thus, according to a further aspect of the present invention there is provided a third process C for the preparation compound of general formula (Ia)

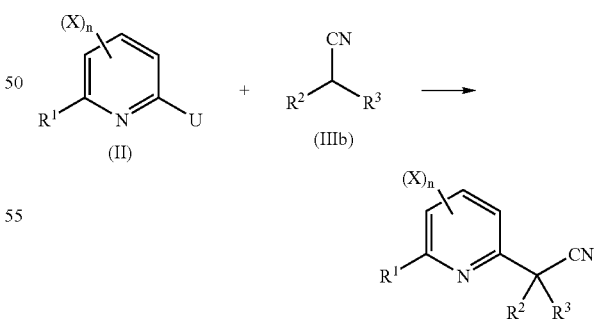

wherein R$^1$, R$^2$, R$^3$, R$^7$, X, Y, n and p are as defined above;
which comprises
a first step according to reaction scheme C-1:

Scheme C-1 in which: R$^1$, R$^2$, R$^3$, X and n are as defined above;
U is a leaving group chosen as being a halogen atom, a C$_1$-C$_6$ alkylsulfonate or a C$_1$-C$_6$ haloalkylsulfonate;

comprising the arylation of a compound of general formula (IIIb) by a pyridine derivative of general formula (II) to provide a 2-pyridylacetonitrile derivative of general formula (Vb), in the presence of a base and at a at temperature of from −100° C. to 200° C.;
a second step according to reaction scheme C-2:

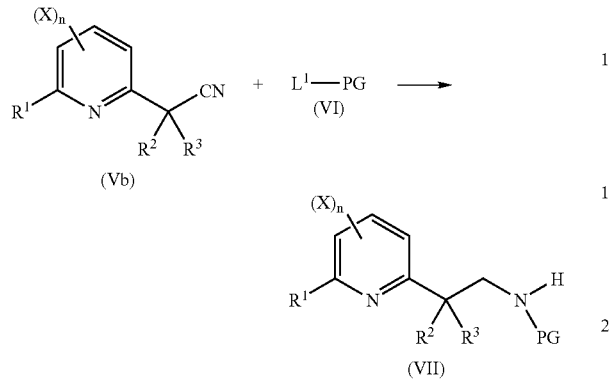

in which:
R$^1$, R$^2$, R$^3$, X and n are as defined above;
L$^1$ is a leaving group chosen as being a —OR$^8$ group or a —OCOR$^8$ group, R$^8$ being a C$_1$-C$_6$ alkyl, a C$_1$-C$_6$ haloalkyl, a benzyl, 4-methoxybenzyl or pentafluorophenyl;
PG represents a protecting group which may be a —COOR$^8$ group or —COR$^8$ group, R$^8$ being a C$_1$-C$_6$ alkyl, a C$_1$-C$_6$ haloalkyl, a benzyl, 4-methoxybenzyl or pentafluorophenyl;

comprising the reduction, by hydrogenation or by an hydride donor, of a compound of general formula (Va) or (Vb), in the presence of a compound of general formula (VI) to produce a compound of general formula (VII);
a third step according to reaction scheme C-3:

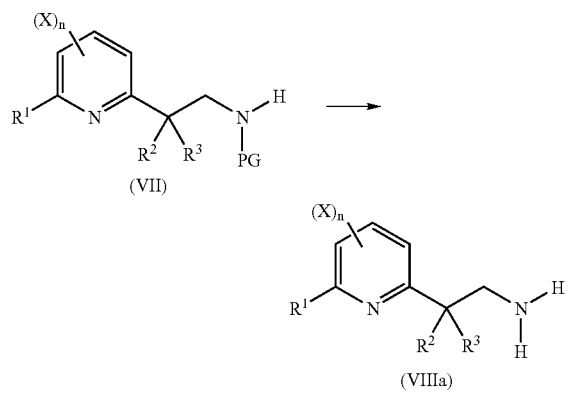

in which: R$^1$, R$^2$, R$^3$, X and n are as defined above;
PG represents a protecting group which may be a —COOR$^8$ group or —COR$^8$ group, R$^8$ being a C$_1$-C$_6$ alkyl, a C$_1$-C$_6$ haloalkyl, a benzyl, 4-methoxybenzyl or pentafluorophenyl;
comprising a deprotection reaction, in an acidic or in a basic medium, of a compound of general formula (VII) to provide an amine derivative of general formula (VIIIa) or one of its salt;

a fourth step according to reaction scheme C-4:

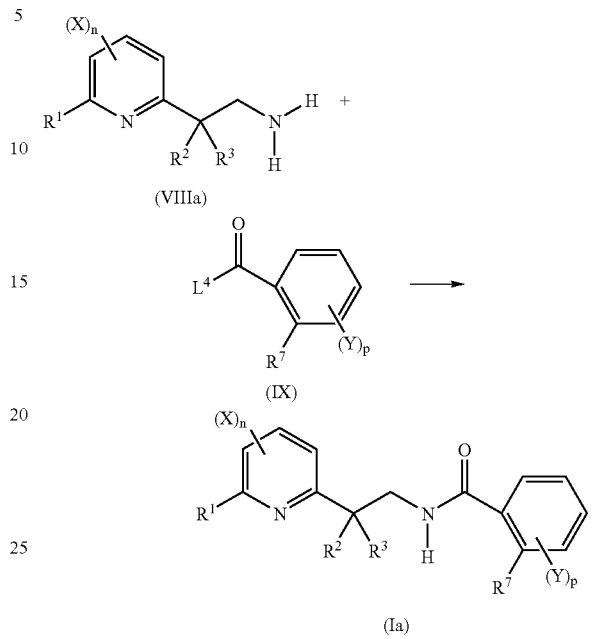

in which: R$^1$, R$^2$, R$^3$, R$^7$, X, Y, n and p are as defined above;
L$^4$ is a leaving group chosen as being a halogen atom, a hydroxyl group, —OCHO, —SCSN(Me)$_2$, an OR$^8$ group, an OCOR$^8$, R$^8$ being a C$_1$-C$_6$ haloalkyl, a benzyl, 4-methoxybenzyl or pentafluorophenyl; or a group of formula

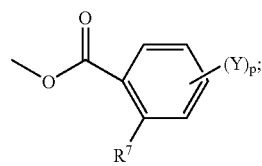

comprising a coupling reaction of an amine derivative of general formula (VIIIa) or one of its salt, with a carboxylic acid derivative of formula (IX) to provide a compound of general formula (Ia).

The first step (step C-1) of the process C according to the present invention is conducted at a temperature of from −100° C. to 200° C. Preferably, first step (step A-1) is conducted at a temperature of from −80° C. to 120° C., more preferably at a temperature of from −80° C. to 80° C.

The first step (step C-1) of the process C according to the present invention is conducted in the presence of a base. Preferably, the base will be chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The first step (step C-1) of the process C according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step C-1) of the process C according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(−)-1-[(S)-2-(dicyclohexylphosphino)ferrocenyl]ethyldicyclohexylphosphine and its corresponding enantiomer, or a mixture of both; (R)-(−)-1[(S)-2-(dicyclohexylphosphino)ferrocenyl]ethyldiphenylphosphine and its corresponding enantiomer, or a mixture of both; (R)-(−)-1[(S)-2-(diphenylphoshino)ferrocenyl]ethyldi-t-butylphosphine and its corresponding enantiomer, or a mixture of both; or (R)-(−)-1[(S)-2-(diphenylphosphino)ferrocenyl]ethyldicyclohexylphosphine and its corresponding enantiomer, or a mixture of both.

The preferred conditions under which step C-2 of the process C is conducted are the same than the preferred conditions under which step A-4 of the above mentioned process A is conducted.

The preferred conditions under which step C-3 of the process C is conducted are the same than the preferred conditions under which step A-5 of the above mentioned process A is conducted.

The preferred conditions under which step C-4 of the process C is conducted are the same than the preferred conditions under which step A-6 of the above mentioned process A is conducted.

The present invention also relates to another process for the preparation of the compound of general formula (I). Thus, according to a further aspect of the present invention there is provided a fourth process D for the preparation of compound of general formula (Ia)

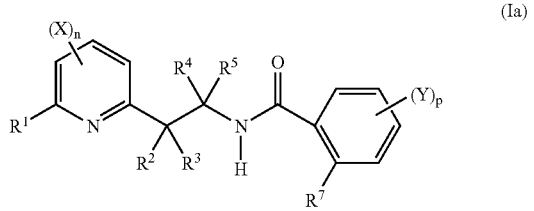

(Ia)

wherein: $R^1$, $R^2$, $R^7$, X, Y, n and p are as defined above; $R^3$ is a $C_1$-$C_6$ alkyl;

which comprises
a first step according to reaction scheme D-1:

Scheme D-1

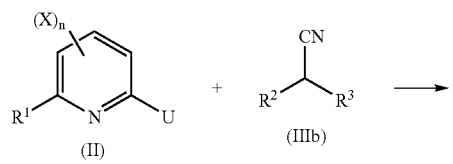

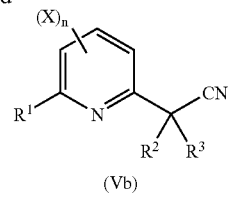

(Vb)

in which: $R^1$, $R^2$, $R^3$, X and n are as defined above;
U is a leaving group chosen as being a halogen atom, a $C_1$-$C_6$ alkylsulfonate or a $C_1$-$C_6$ haloalkylsulfonate;

comprising the arylation of a compound of general formula (IIIb) by a pyridine derivative of general formula (II) to provide a 2-pyridylacetonitrile derivative of general formula (Vb), in the presence of a base and at a at temperature of from −100° C. to 200° C.;

a second step according to reaction scheme D-2:

Scheme D-2

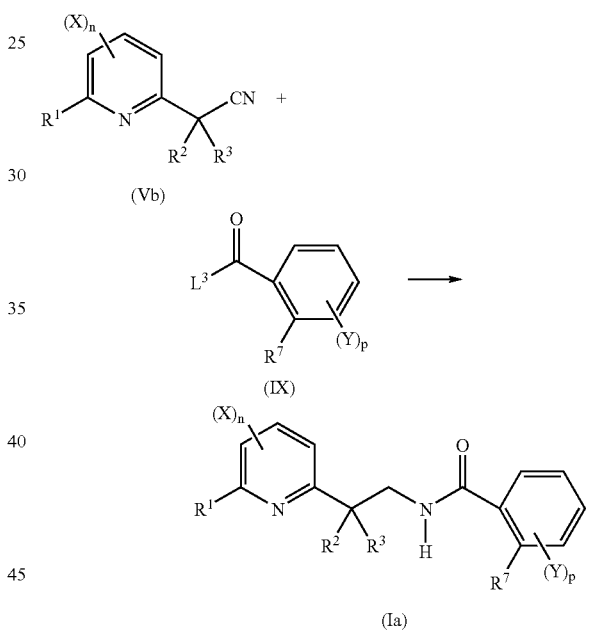

in which:
$R^1$, $R^2$, $R^7$, X, Y, n and p are as defined above;
$R^3$ is a $C_1$-$C_6$ alkyl;
$L^3$ is a leaving group chosen as being —OCOR$^8$, $R^8$ being a $C_1$-$C_6$ alkyl, a $C_1$-$C_6$ haloalkyl, a benzyl, 4-methoxybenzyl or pentafluorophenyl; —OCHO, —SCSN(Me)$_2$ or a group of formula

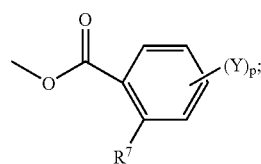

comprising the reduction by hydrogenation or by an hydride donor a compound of general formula (Va) or a compound of general formula (Vb) in the presence of a compound of general formula (IX) to provide a compound of general formula (Ia).

Compound of general formula (Ia) according to the present invention may be prepared according to the process D.

The preferred conditions under which step D-1 of the process D is conducted are the same than the preferred conditions under which step C-1 of the above mentioned process C is conducted.

The preferred conditions under which step D-2 of the process D is conducted are the same than the preferred conditions under which step A-4 of the above mentioned process A is conducted.

The present invention also relates to a process for the preparation of the compound of general formula (I). Thus, according to a further aspect of the present invention there is provided a fifth process (E) for the preparation of compound of general formula (Ia)

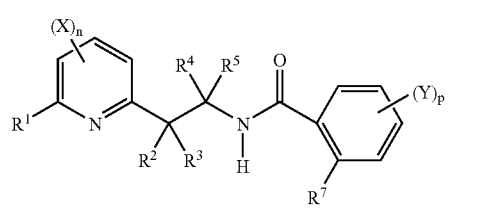

(Ia)

wherein:
$R^1$, $R^2$, $R^3$, $R^7$, X, Y, n and p are as defined above;
$R^4$ is a hydrogen atom, a $C_1$-$C_6$ alkyl or a $C_1$-$C_6$ haloalkyl;
$R^5$ is a $C_1$-$C_6$ alkyl or a $C_1$-$C_6$ haloalkyl; $L^4$ is a leaving group chosen as being a halogen atom, a hydroxyl group, —OCHO, —SCSN(Me)$_2$, an $OR^8$ group, an $OCOR^8$, $R^8$ being a $C_1$-$C_6$ alkyl, a $C_1$-$C_6$ haloalkyl, a benzyl, 4-methoxybenzyl or pentafluorophenyl; or a group of formula

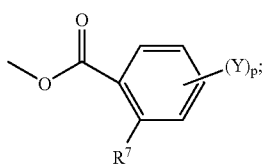

which comprises
a first step according to reaction scheme E-1:

Scheme E-1

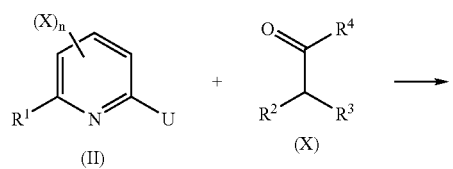

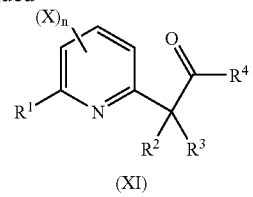

(XI)

in which:
$R^1$, $R^2$, $R^3$, X and n are as defined above;
$R^4$ is a hydrogen atom, a $C_1$-$C_6$ alkyl or a $C_1$-$C_6$ haloalkyl;
U is a leaving group chosen as being a halogen atom, a $C_1$-$C_6$ alkylsulfonate or a $C_1$-$C_6$ haloalkylsulfonate;
comprising the arylation of a compound of general formula (X) by a pyridine derivative of general formula (II) to provide a compound of general formula (XI);
a second step according to reaction scheme E-2:

Scheme E-2

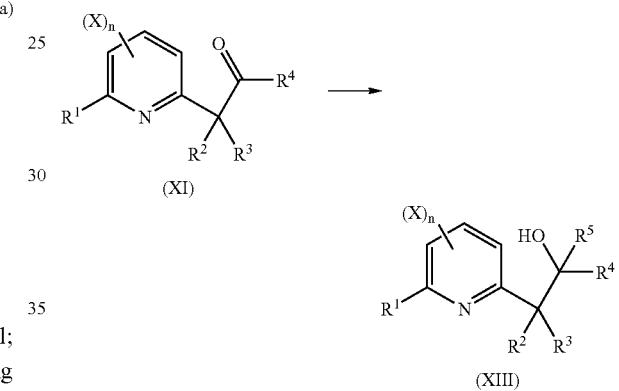

in which: $R^1$, $R^2$, $R^3$, X and n are as defined above;
$R^4$ is a hydrogen atom, a $C_1$-$C_6$ alkyl or a $C_1$-$C_6$ haloalkyl;
comprising the conversion of a compound of general formula (XI) into a compound of general formula (XIII) by addition of a compound of general formula $R^5$-M, in which $R^5$ is a $C_1$-$C_6$ alkyl or a $C_1$-$C_6$ haloalkyl and M is a metal specie;
a third step according to reaction scheme E-3:

Scheme E-3

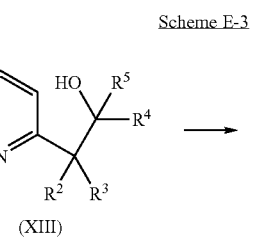

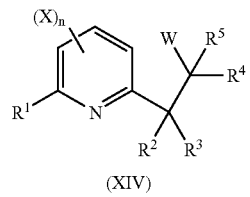

(XIV)

in which:
 $R^1$, $R^2$, $R^3$, X and n are as defined above;
 $R^4$ is a hydrogen atom, a $C_1$-$C_6$ alkyl or a $C_1$-$C_6$ haloalkyl;
 $R^5$ is a $C_1$-$C_6$ alkyl or a $C_1$-$C_6$ haloalkyl;
 W is a leaving group chosen as being a halogen atom, a $C_1$-$C_6$ alkylsulfonate, a $C_1$-$C_6$ haloalkylsulfonate or a 4-methyl-phenylsulfonate;
comprising the activation of a compound of general formula (XIII) by converting it into a compound of general formula (XIV);
a fourth step according to reaction scheme E-4:

Scheme E-4

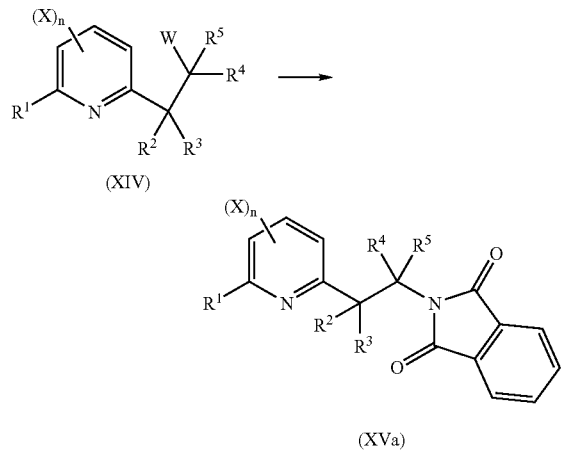

(XIV)

(XVa)

in which:
 $R^1$, $R^2$, $R^3$, X and n are as defined above;
 $R^4$ is a hydrogen atom, a $C_1$-$C_6$ alkyl or a $C_1$-$C_6$ haloalkyl;
 $R^5$ is a $C_1$-$C_6$ alkyl or a $C_1$-$C_6$ haloalkyl;
 W is a leaving group chosen as being a halogen atom, a $C_1$-$C_6$ alkylsulfonate, a $C_1$-$C_6$ haloalkylsulfonate or a 4-methyl-phenylsulfonate;
comprising the substitution of a compound of general formula (XIV) by a phtalimide derivative or one of its salt to provide a compound of general formula (XVa);
a fifth step according to reaction scheme E-5:

Scheme E-5

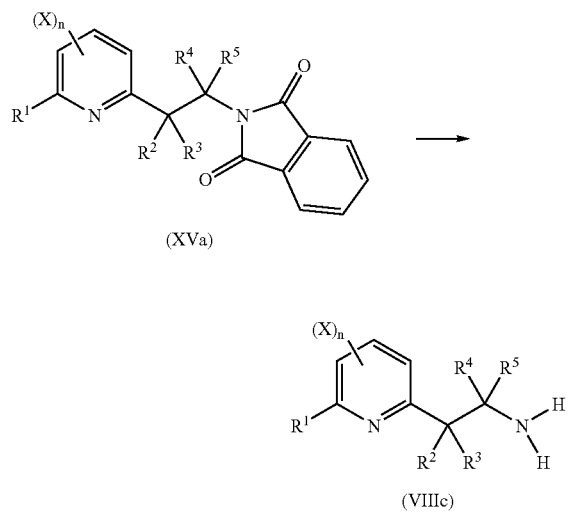

(XVa)

(VIIIc)

in which:
 $R^1$, $R^2$, $R^3$, X and n are as defined above;
 $R^4$ is a hydrogen atom, a $C_1$-$C_6$ alkyl or a $C_1$-$C_6$ haloalkyl;
 $R^5$ is a $C_1$-$C_6$ alkyl or a $C_1$-$C_6$ haloalkyl;
comprising the de-protection of a compound of general formula (XVa) by reacting it with hydrazine hydrate or a hydrazine salt to provide an amine derivative of general formula (VIIIc) or one of its salt;
a sixth step according to reaction scheme E-6:

Scheme E-6

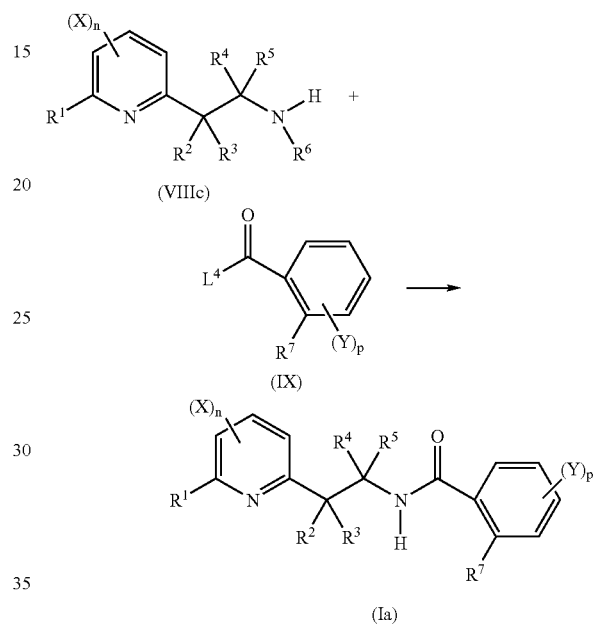

(VIIIc)

(IX)

(Ia)

in which:
 $R^1$, $R^2$, $R^3$, $R^7$, X, Y, n and p are as defined above;
 $R^4$ is a hydrogen atom, a $C_1$-$C_6$ alkyl or a $C_1$-$C_6$ haloalkyl;
 $R^5$ is a $C_1$-$C_6$ alkyl or a $C_1$-$C_6$ haloalkyl; $L^4$ is a leaving group chosen as being a halogen atom, a hydroxyl group, —OCHO, —SCSN(Me)$_2$, an $OR^8$ group, an $OCOR^8$, $R^8$ being a $C_1$-$C_6$ alkyl, a $C_1$-$C_6$ haloalkyl, a benzyl, 4-methoxybenzyl or pentafluorophenyl; or a group of formula

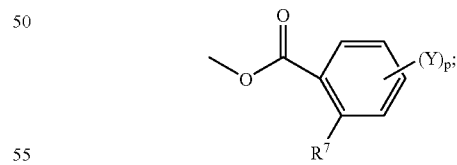

comprising a coupling reaction of an amine derivative of general formula (VIIIb) or one of its salt, with a carboxylic acid derivative of formula (IX) to provide a compound of general formula (Ia).

Compound of general formula (I) according to the present invention may be prepared according to the process E.

The preferred conditions under which step E-6 of the process E is conducted are the same than the preferred conditions under which step A-6 of the above mentioned process A is conducted.

The present invention also relates to another process for the preparation of the compound of general formula (I). Thus, according to a further aspect of the present invention there is provided a sixth process F for the preparation of compound of general formula (Ia)

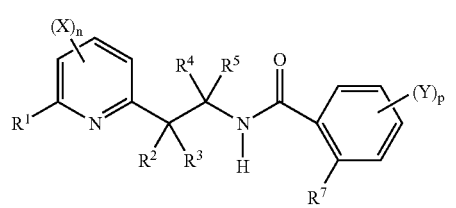

wherein: $R^1$, $R^7$, X, Y, n and p are as defined above;
$R^2$, $R^4$ and $R^5$ are independently from each other chosen as being a hydrogen atom, a $C_1$-$C_6$ alkyl or a $C_1$-$C_6$ haloalkyl;

which comprises
a first step according to reaction scheme F-1:

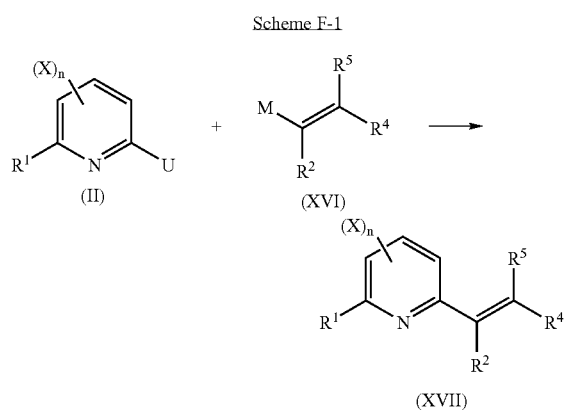

in which: $R^1$, X and n are as defined above;
U is a leaving group chosen as being a halogen atom a $C_1$-$C_6$ alkylsulfonate or a $C_1$-$C_6$ haloalkylsulfonate;
$R^2$, $R^4$ and $R^5$ are independently from each other chosen as being a hydrogen atom, a $C_1$-$C_6$ alkyl or a $C_1$-$C_6$ haloalkyl;
M is a metal or a metalloid specie;

comprising a coupling reaction of a pyridine derivative of general formula (II) with a vinylic specie of general formula (XVI), at a temperature of from 0° C. to 200° C., to provide a compound of general formula (XVII);
a second step according to reaction scheme F-2:

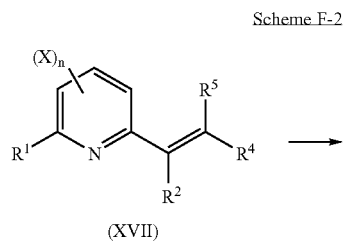

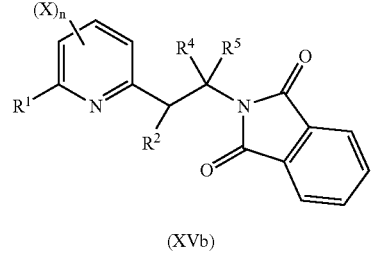

in which: $R^1$, X and n are as defined above;
$R^2$, $R^4$ and $R^5$ are independently from each other chosen as being a hydrogen atom, a $C_1$-$C_6$ alkyl or a $C_1$-$C_6$ haloalkyl;

comprising the addition of a phtalimide or one of its salt on a compound of general formula (XVII) to provide a compound of general formula (XVb);
a third step according to reaction scheme F-3:

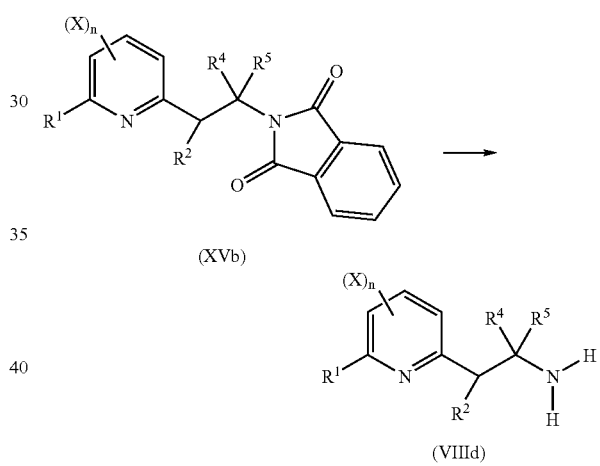

in which: $R^1$, X and n are as defined above;
$R^2$, $R^4$ and $R^5$ are independently from each other chosen as being a hydrogen atom, a $C_1$-$C_6$ alkyl or a $C_1$-$C_6$ haloalkyl;

comprising the de-protection of a compound of general formula (XVb) with hydrazine hydrate or an hydrazine salt, to provide an amine derivative of general formula (VIIId) or one of its salts;
a fourth step according to reaction scheme F-4:

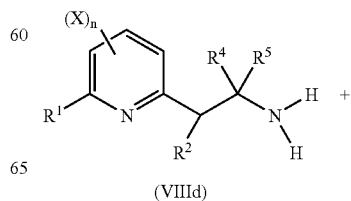

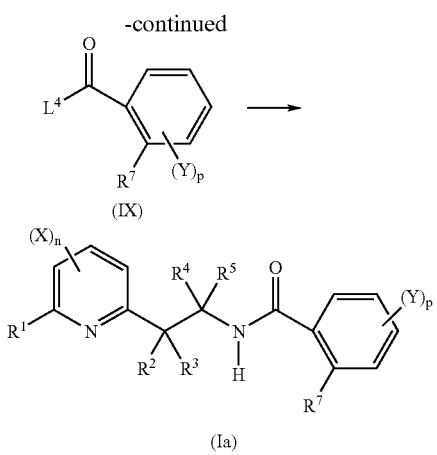

in which:
R¹, R⁷, X, Y, n and p are as defined above;
R², R⁴ and R⁵ are independently from each other chosen as being a hydrogen atom, a $C_1$-$C_6$ alkyl or a $C_1$-$C_6$ haloalkyl;
L⁴ is a leaving group chosen as being a halogen atom, a hydroxyl group, —OCHO, —SCSN(Me)₂, an OR⁸ group, an OCOR⁸, R⁸ being a $C_1$-$C_6$ alkyl, a $C_1$-$C_6$ haloalkyl, a benzyl, 4-methoxybenzyl or pentafluorophenyl; or a group of formula

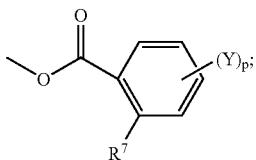

comprising a coupling reaction of an amine derivative of general formula (VIIIb) or one of its salt, with a carboxylic acid derivative of formula (IX) to provide a compound of general formula (Ia).

The first step (step F-1) of the process F according to the present invention is conducted in the presence of a vinylic specie of general formula (XVI) in which M can be a metal or a metalloid specie. Preferably M is a tin derivative or a boron derivative. More preferably M is a tri-nbutyltin group.

The first step (step F-1) of the process F according to the present invention is conducted at a temperature of from 0° C. to 200° C. Preferably, step G-1 is conducted at a temperature of from 60° C. to 160° C., more preferably at temperature of from 80° C. to 140° C.

The first step (step F-1) of the process F according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step F-1) of the process F according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(–)-1-[(S)-2-(dicyclohexylphosphino)ferrocenyl]ethyl-dicyclohexylphosphine and its corresponding enantiomer, or a mixture of both; (R)-(–)-1[(S)-2-(dicyclohexylphosphino) ferrocenyl]ethyldiphenylphosphine and its corresponding enantiomer, or a mixture of both; (R)-(–)-1[(S)-2-(diphenylphosphino)ferrocenyl]ethyldi-t-butylphosphine and its corresponding enantiomer, or a mixture of both; or (R)-(–)-1[(S)-2-(diphenylphosphino)ferrocenyl]ethyldicyclohexylphosphine and its corresponding enantiomer, or a mixture of both.

The first step (step F-1) of the process F according to the present invention may also be conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The preferred conditions under which step F-3 of the process F is conducted are the same than the preferred conditions under which step E-5 of the above mentioned process E is conducted.

The preferred conditions under which step F-4 of the process F is conducted are the same than the preferred conditions under which step A-6 of the above mentioned process A is conducted.

Any of the above described processes A to F may optionally comprise a further step according to reaction scheme G:

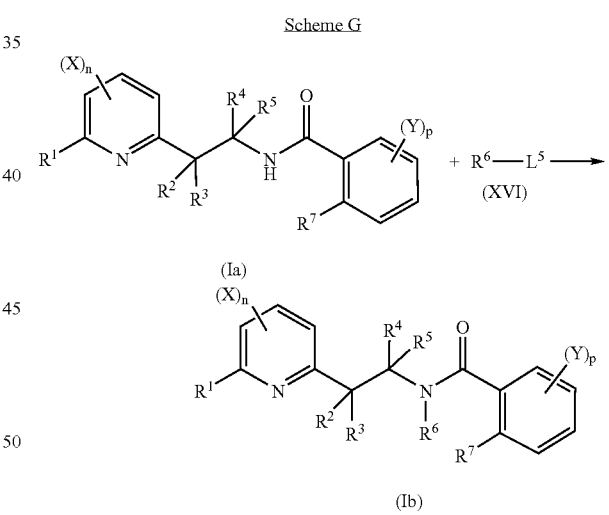

in which: R¹, R², R³, R⁴, R⁵, R⁶, R⁷, X, Y, n and p are as defined above;
L⁵ is a leaving group chosen as being a halogen atom, a 4-methyl phenylsulfonyloxy, a methylsulfonyloxy;

comprising the reaction of a compound of general formula (Ia) with a compound of general formula (XVI) to provide a compound of general formula (Ib).

The present invention also relates to another process for the preparation of the compound of general formula (I). Thus, according to a further aspect of the present invention there is provided a seventh process H for the preparation of compound of general formula (I) as defined above, which comprises
a first step according to reaction scheme H-1:

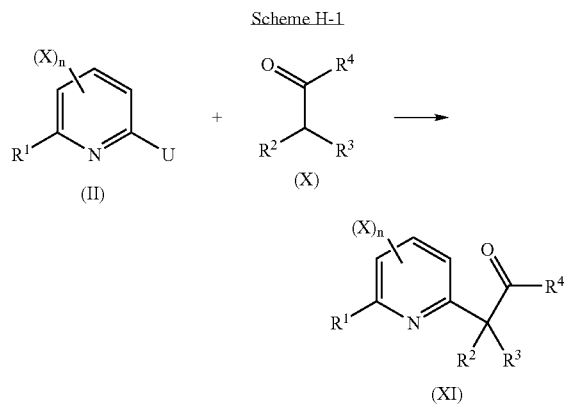

Scheme H-1

(II) + (X) → (XI)

in which:
R$^1$, R$^2$, R$^3$, X and n are as defined above;
R$^4$ is a hydrogen atom, a C$_1$-C$_6$ alkyl or a C$_1$-C$_6$ haloalkyl;
U is a leaving group chosen as being a halogen atom, a C$_1$-C$_6$ alkylsulfonate or a C$_1$-C$_6$ haloalkylsulfonate;

comprising the arylation of a compound of general formula (X) by a pyridine derivative of general formula (II) to provide a compound of general formula (XI), in the presence of a base, at a temperature of from 0° C. to 200° C.;

a second step according to reaction scheme H-2:

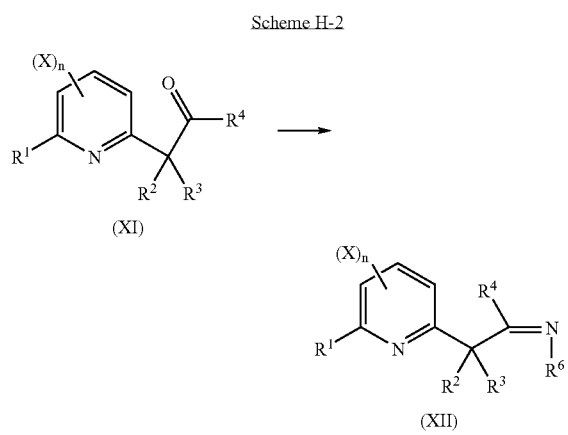

Scheme H-2

(XI) → (XII)

in which:
R$^1$, R$^2$, R$^3$, X and n are as defined above;
R$^4$ is a hydrogen atom, a C$_1$-C$_6$ alkyl or a C$_1$-C$_6$ haloalkyl;
R$^6$ is a hydrogen atom, a C$_1$-C$_6$ alkyl, a C$_1$-C$_6$ haloalkyl, a C$_1$-C$_6$ alkoxy or a C$_3$-C$_7$ cycloalkyl;

comprising the reaction of a compound of general formula (XI) with an amine of formula R$^6$—NH2 to provide an imine derivative of general formula (XII);

a third step according to scheme H-3:

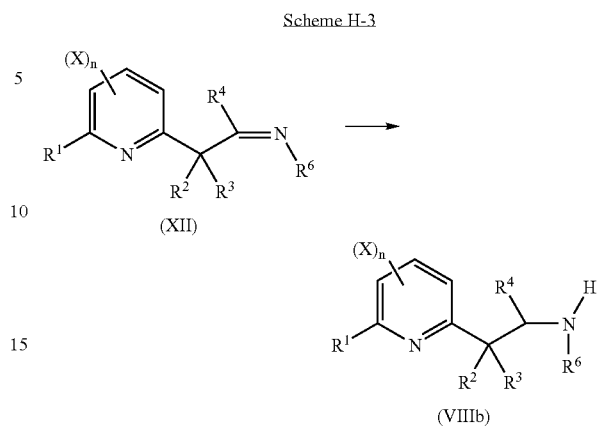

Scheme H-3

(XII) → (VIIIb)

in which:
R$^1$, R$^2$, R$^3$, X and n are as defined above;
R$^4$ is a hydrogen atom, a C$_1$-C$_6$ alkyl or a C$_1$-C$_6$ haloalkyl;
R$^6$ is a hydrogen atom, a C$_1$-C$_6$ alkyl, a C$_1$-C$_6$ haloalkyl, a C$_1$-C$_6$ alkoxy or a C$_3$-C$_7$ cycloalkyl;

comprising the reduction of an imine derivative of general formula (XII) by hydrogenation or by an hydride donor, in the same or a different pot to provide an amine derivative of general formula (VIIIb) or one of its salt;

a fourth step according to reaction scheme H-4:

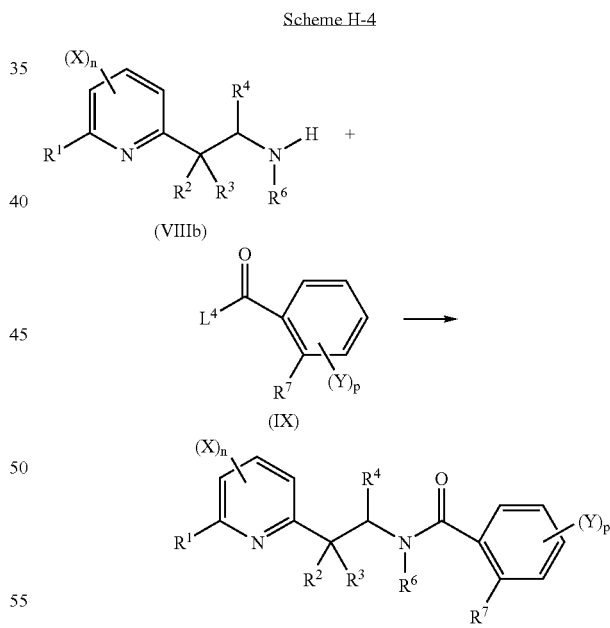

Scheme H-4

(VIIIb) + (IX) → (I)

in which:
R$^1$, R$^2$, R$^3$, R$^7$, X, Y, n and p are as defined above;
R$^4$ is a hydrogen atom, a C$_1$-C$_6$ alkyl or a C$_1$-C$_6$ haloalkyl;
R$^6$ is a hydrogen atom, a C$_1$-C$_6$ alkyl, a C$_1$-C$_6$ haloalkyl, a C$_1$-C$_6$ alkoxy or a C$_3$-C$_7$ cycloalkyl;
L$^4$ is a leaving group chosen as being a halogen atom, a hydroxyl group, —OCHO, —SCSN(Me)$_2$, an OR$^8$ group, an OCOR$^8$, R$^8$ being a C$_1$-C$_6$ alkyl, a C$_1$-C$_6$ haloalkyl, a benzyl, 4-methoxybenzyl or pentafluorophenyl; or a group of formula

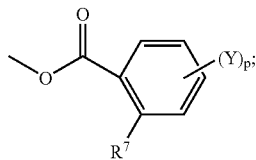

comprising a coupling reaction of an amine derivative of general formula (VIIIb) or one of its salt, with a carboxylic acid derivative of formula (IX) to provide a compound of general formula (I).

Compound of general formula (I) according to the present invention may be prepared according to the process H.

The preferred conditions under which step H-1 of the process H is conducted are the same than the preferred conditions under which step A-1 of the above mentioned process A is conducted.

The third step (step H-3) of the process H according to the present invention is conducted in the presence of a hydride donor. Preferably, the hydride donor is chosen as being metal or metalloid hydrides such as $LiAlH_4$, $NaBH_4$, $KBH_4$, $B_2H_6$.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesise.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterized in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of: cotton; flax; vine; fruit or vegetable crops such as Rosaceae sp. (for instance pip fruits such as apples and pears, but also stone fruits such as apricots, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruits); leguminous crops such as Solanaceae sp. (for instance tomatoes), Liliaceae sp., Asteraceae sp. (for instance lettuces), Umbelliferae sp., Cruciferae sp., Chenopodiaceae sp., Cucurbitaceaeo sp., Papilionaceae sp. (for instance peas), Rosaceae sp. (for instance strawberries); big crops such as Graminae sp. (for instance maize, lawn or cereals such as wheat, rice, barley and triticale), Asteraceae sp. (for instance sunflower), Cruciferae sp. (for instance colza), Papilionaceae sp. (for instance soja), Solanaceae sp. (for instance potatoes), Chenopodiaceae sp. (for instance beetroots); horticultural and forest crops; as well as genetically modified homologues of these crops.

Among the plants and the possible diseases of these plants protected by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* forma specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* forma specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Sclerotinia sclerotiorum*;

corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola*;

forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, trichophyton diseases and candidiases or diseases caused by *Aspergillus* spp., for example *Aspergillus fumigatus*.

The aspects of the present invention will now be illustrated with reference to the following tables of compounds and examples. The following Table illustrates in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy and M (ApcI+) means the molecular ion peak as it was found via positive atmospheric pressure chemical ionisation in mass spectroscopy.

| Compound n° | $X^1$ | $X^2$ | $X^3$ | $R^1$ | $R^2$ | $R^3$ | $R^4$ | $R^5$ | $R^6$ | $R^7$ | $Y^1$ | $Y^2$ | $Y^3$ | $Y^4$ | M | (M + 1) |
|---|---|---|---|---|---|---|---|---|---|---|---|---|---|---|---|---|
| 1 | Cl | H | Cl | H | H | H | H | H | H | CF$_3$ | H | H | H | H | — | 363 |
| 2 | Cl | H | Cl | H | H | H | H | H | H | Cl | H | H | H | H | — | 329 |
| 3 | Cl | H | Cl | H | H | H | H | H | H | CH$_3$ | H | H | H | H | — | 309 |
| 4 | Cl | H | Cl | H | H | H | H | H | H | Br | H | H | H | H | — | 374 |
| 5 | Cl | H | Cl | H | H | H | H | H | H | I | H | H | H | H | — | 421 |
| 6 | H | H | Cl | H | H | H | H | H | H | CF$_3$ | H | H | H | H | — | 329 |
| 7 | Cl | H | H | H | Me | H | H | H | H | Cl | H | F | H | H | 327 | — |
| 8 | CH$_3$ | H | Br | H | H | H | H | H | H | CF$_3$ | H | H | H | H | — | 388 |
| 9 | CH$_3$ | H | H | H | H | H | H | H | H | CF$_3$ | H | H | H | H | — | 309 |
| 10 | Cl | H | F | H | H | H | H | H | H | CF$_3$ | H | H | H | H | — | 347 |
| 11 | Cl | H | F | H | H | H | H | H | H | Br | H | H | H | H | — | 358 |
| 12 | F | H | F | F | H | H | H | H | H | CF$_3$ | H | H | H | H | — | 349 |
| 13 | H | H | Cl | F | H | H | H | H | H | CF$_3$ | H | H | H | H | — | 347 |
| 14 | CH$_3$ | H | H | H | H | H | H | H | H | I | H | H | H | H | — | 367 |
| 15 | C(Me)=NOMe | H | Cl | H | H | H | H | H | H | Cl | H | H | H | H | — | 366 |
| 16 | C(Me)=NOMe | H | Cl | H | H | H | H | H | H | I | H | H | H | H | — | 458 |
| 17 | C(Me)=NOMe | H | Cl | H | H | H | H | H | H | CF$_3$ | H | H | H | H | — | 400 |
| 18 | Br | H | CH$_3$ | H | H | H | H | H | H | CF$_3$ | H | H | H | H | — | 387 |
| 19 | Br | H | H | H | H | H | H | H | H | CF$_3$ | H | H | H | H | — | 374 |
| 20 | Cl | H | H | H | H | H | H | H | H | CF$_3$ | H | H | H | H | — | 329 |
| 21 | Cl | H | F | H | H | H | H | H | H | I | H | H | H | H | — | 405 |
| 22 | Cl | H | Cl | Cl | H | H | H | H | H | I | H | H | H | H | — | 455 |
| 23 | Cl | H | Cl | Cl | H | H | H | H | H | CF3 | H | H | H | H | — | 397 |
| 24 | Cl | H | H | H | H | H | H | H | H | I | H | H | H | H | — | 387 |
| 25 | CH=NOMe | H | Cl | H | H | H | H | H | H | I | H | H | H | H | — | 444 |
| 26 | CH=NOMe | H | Cl | H | H | H | H | H | H | CF$_3$ | H | H | H | H | — | 386 |
| 27 | CH=NOEt | H | Cl | H | H | H | H | H | H | I | H | H | H | H | — | 458 |
| 28 | CH=NOEt | H | Cl | H | H | H | H | H | H | CF$_3$ | H | H | H | H | — | 400 |
| 29 | Cl | H | F | H | H | H | H | H | H | CHF$_2$ | H | H | H | H | — | 329 |
| 30 | CH=NOiPr | H | Cl | H | H | H | H | H | H | CF$_3$ | H | H | H | H | — | 414 |
| 31 | CH=NOiPr | H | Cl | H | H | H | H | H | H | I | H | H | H | H | — | 472 |
| 32 | CH=NOiPr | H | Cl | H | H | H | H | H | H | Br | H | H | H | H | — | 424 |
| 33 | CH=NOiPr | H | Cl | H | H | H | H | H | H | CHF$_2$ | H | H | H | H | — | 396 |
| 34 | Cl | H | Cl | F | H | H | H | H | H | I | H | H | H | H | — | 439 |
| 35 | H | H | Cl | Cl | H | H | H | H | H | CF$_3$ | H | H | H | H | — | 363 |
| 36 | H | H | Cl | Cl | H | H | H | H | H | I | H | H | H | H | — | 421 |
| 37 | H | H | Cl | Cl | H | H | H | H | H | Br | H | H | H | H | — | 375 |
| 38 | Cl | H | Br | H | H | H | H | H | H | CF$_3$ | H | H | H | H | — | 407 |
| 39 | Cl | H | H | H | H | H | H | H | H | Br | H | H | H | H | — | 339 |
| 40 | Cl | H | Br | H | H | H | H | H | H | I | H | H | H | H | — | 465 |
| 41 | H | H | Cl | Cl | H | H | H | H | H | CHF$_2$ | H | H | H | H | — | 345 |
| 42 | F | Me | F | F | H | H | H | H | H | CF$_3$ | H | H | H | H | — | 363 |
| 43 | F | Me | F | F | H | H | H | H | H | I | H | H | H | H | — | 421 |
| 44 | F | Me | F | F | H | H | H | H | H | Br | H | H | H | H | — | 374 |
| 45 | F | H | F | F | H | H | H | H | H | I | H | H | H | H | — | 407 |
| 46 | Cl | H | F | H | H | H | H | H | H | CHF$_2$ | H | H | H | H | — | 329 |
| 47 | F | H | F | F | H | H | H | H | H | Br | H | H | H | H | — | 359 |
| 48 | F | H | F | F | H | H | H | H | H | Cl | H | H | H | H | — | 315 |
| 49 | F | Me | F | F | H | H | H | H | H | Me | H | H | H | H | — | 309 |
| 50 | Br | H | Cl | H | H | H | H | H | H | CF$_3$ | H | H | H | H | — | 406 |
| 51 | Br | H | Cl | H | H | H | H | H | H | I | H | H | H | H | — | 466 |

-continued

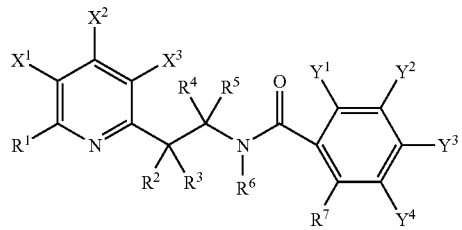

| Compound n° | X¹ | X² | X³ | R¹ | R² | R³ | R⁴ | R⁵ | R⁶ | R⁷ | Y¹ | Y² | Y³ | Y⁴ | M | (M + 1) |
|---|---|---|---|---|---|---|---|---|---|---|---|---|---|---|---|---|
| 52 | Br | H | Cl | H | H | H | H | H | H | Br | H | H | H | H | — | 419 |
| 53 | Cl | H | Cl | Me | H | H | H | H | H | CF₃ | H | H | H | H | — | 376 |
| 54 | Cl | H | Cl | Me | H | H | H | H | H | I | H | H | H | H | — | 434 |
| 55 | Cl | H | Cl | Me | H | H | H | H | H | Br | H | H | H | H | — | 386 |
| 56 | H | H | Cl | Me | H | H | H | H | H | CF₃ | H | H | H | H | — | 343 |
| 57 | Cl | H | Cl | F | H | H | H | H | H | CF₃ | H | H | H | H | — | 381 |
| 58 | Cl | H | Cl | F | H | H | H | H | H | Br | H | H | H | H | — | 391 |
| 59 | Cl | H | Cl | F | H | H | H | H | H | Cl | H | H | H | H | — | 347 |
| 60 | Cl | H | Cl | H | Me | H | H | H | H | CF₃ | H | H | H | H | 377 | — |
| 61 | Cl | H | Cl | H | Me | H | H | H | H | I | H | H | H | H | 435 | — |
| 62 | Cl | H | F | F | H | H | H | H | H | CF₃ | H | H | H | H | — | 365 |
| 63 | Cl | H | F | F | H | H | H | H | H | I | H | H | H | H | — | 423 |
| 64 | F | H | F | F | H | H | H | H | H | CHF₂ | H | H | H | H | — | 331 |
| 65 | Cl | H | H | H | Me | H | H | H | H | I | H | H | H | H | — | 401 |
| 66 | Cl | H | H | H | Me | H | H | H | H | CF₃ | H | H | H | H | — | 343 |
| 67 | Cl | H | Cl | H | cPr | H | H | H | H | CF₃ | H | H | H | H | — | 389 |
| 68 | Cl | H | H | H | cPr | H | H | H | H | CF₃ | H | H | H | H | — | 355 |
| 69 | Cl | H | Cl | pCl—Ph—CH₂S | H | H | H | H | H | CF₃ | H | H | H | H | — | 519 |
| 70 | Cl | H | H | H | Me | H | H | H | H | Cl | Cl | H | F | H | 327 | — |

EXAMPLES OF PROCESS FOR THE PREPARATION OF THE COMPOUND OF GENERAL FORMULA (I)

Example of Process A

Preparation of N-[2-(3,5-dichloro-2-pyridinyl)ethyl]-2-(iodo)benzamide (compound 5)

Step 1: Preparation of ter-butyl cyano(3,5-dichloro-2-pyridinyl)acetate

To 50 ml of dimethoxyethane was slowly added portionwise at 0° C., 8.8 g (0.22 mol) of sodium hydride (60% dispersion in mineral oil).

To this suspension, was further added dropwise at 5° C., 17 g (0.12 mol) of ter-butyl cyanoacetate in 50 ml of dimethoxyethane. The suspension was stirred for 45 mn at room temperature.

To the suspension were successively added 20 g (0.11 mol) of 2,3,5-trichloropyridine, 0.59 g (1.1 mmol) of (S)-(+)-1-[(R)-2-(diphenylphosphino)ferrocenyl]ethyl-ter-butylphosphine, and 1.2 g (2.2 mmol) of bis(dibenzylideneacetone)palladium(0).

The black mixture was heated at reflux for 5 hours. After cooling, the reaction mixture was poured into 100 ml of 1N hydrochloric acid. The aqueous phase was filtered on supersel and was extracted with ethyl acetate (3×200 ml). The organic phase was washed with brine and dried over magnesium sulphate. The solvent was evaporated under reduced pressure to give 38.5 g of the crude product as a brown oil.

The crude product was purified by flash chromatography on silica gel (eluent: heptane/chloroforme: 6/4) to give ter-butyl cyano(3,5-dichloro-2-pyridinyl)acetate: 13 g (41%) as a yellow oil; mass spectrum: 287 (M+1).

Step 2: Preparation of (3,5-dichloro-2-pyridinyl)acetonitrile

To a solution of 12 g (0.042 mol) of ter-butyl cyano(3,5-dichloro-2-pyridinyl)acetate in 50 ml of a 25/1 mixture of dimethylsulfoxide/water, was added 1.2 g (0.021 mol) of sodium chloride.

The mixture was stirred for 3 hours at 130° C. After cooling, the reaction mixture was poured into ice water. The aqueous phase was extracted with ethyl acetate (3×250 ml) and the organic phase was washed with brine and dried over magnesium sulphate. The solvent was evaporated under reduced pressure to give 8.2 g of die crude product as a brown oil.

The crude product was purified by flash chromatography on silica gel (eluent: heptane/ethyl acetate: 7/3) to give (3,5-dichloro-2-pyridinyl)acetonitrile: 5.9 g (76%) as an orange oil; mass spectrum: 185 (M−1).

Step 3: Preparation of ter-butyl 2-(3,5-dichloro-2-pyridinyl)ethylcarbamate

To a solution of 2.8 (0.015 mol) of (3,5-dichloro-2-pyridinyl)acetonitrile in 40 ml of methanol were rapidly added 3.9 g (0.0165 mol) of colbalt(II) chloride hexahydrate and 6.5 g (0.03 mol) of di-ter-butyl dicarbonate.

The dark solution was cooled to −5° C. and 3.96 g (0.1 mol) of sodium borohydride was added portion-wise at 0° C. The reaction mixture was stirred at room temperature for 18 hours.

The reaction mixture was neutralized by 1 N hydrochloric acid and methanol was remove under reduced pressure. The aqueous phase was reextracted by dichloromethane and the organic phase was washed with brine and dried over magnesium sulphate. The solvent was evaporated under reduced pressure to give 4 g of the crude product as a brown oil.

The crude product was purified by flash chromatography on silica gel (eluent: heptane/ethyl acetate: 5/1) to give ter-butyl 2-(3,5-dichloro-2-pyridinyl)ethylcarbamate: 2.0 g (46%) as a yellow oil; mass spectrum: 192 (M+1-101 (boc)).

Step 4: Preparation of hydrochlorhide of 2-(3,5-dichloro-2-pyridinyl)ethanamine To a solution of 2.4 g (8.2 mmol) of ter-butyl 2-(3,5-dichloro-2-pyridinyl)ethyl carbamate in 100 ml of dichloromethane were added 5 ml of trifluoroacetique acid.

The mixture was stirred 1 hour at room temperature. The solvent was evaporated under reduced pressure to give 4.7 g of a crude yellow oil.

The crude oil was redissolved in 10 ml of ethyl ether and 5.2 ml of 2 N hydrochloric acid was added dropwise to precipitated the hydrochlorhide.

The solid was collected by filtration, washed by ethyl ether and dried under vacuum to give 2-(3,5-dichloro-2-pyridinyl)ethanamine as its hydrochlorhide: 1.3 g (70%).

Step 5: Preparation of N-[2-(3,5-dichloro-2-pyridinyl)ethyl]-2-(iodo)benzamide (compound 5)

To a suspension of 60 mg (0.26 mmol) of the hydrochlorhide of 2-(3,5-dichloro-2-pyridinyl)ethanamine in 1 ml of dichloromethane was added successively 81 μl (0.58 mmol) of triethylamine and 85 mg (0.32 mmol) of 2-iodobenzoyl chloride. The mixture was stirred 18 hour at room temperature.

The reaction mixture was poured into water and the pH brought to 4. The aqueous phase was extracted with ethyl acetate and the organic phase was washed with brine and dried over magnesium sulphate.

The solvent was evaporated and the residue was purified by flash chromatography on silica gel (eluent: heptane/ethyl acetate: 8/2) to give N-[2-(3,5-dichloro-2-pyridinyl)ethyl]-2-(iodo)benzamide as a brown solid: 47 mg (43%); m.p.=133° C.

The following compounds of formula (I) are prepared according to a process identical to the one used for the preparation of compound 5, and illustrate as well the present invention: 2, 3, 4, 13, 16, 17, 21, 22, 23, 25 and 26.

Example of Process B

Preparation of N-[2-(3,5-dichloro-2-pyridinyl)ethyl]-2-(trifluoromethyl)benzamide (compound 1)

Step 1: Preparation of methyl cyano(3,5-dichloro-2-pyridinyl)acetate

To 100 ml of 1-methyl-2-pyrrolidinone was slowly added portionwise at 0° C., 24.8 g (0.62 mol) of sodium hydride (60% dispersion in mineral oil).

To this suspension, was further added dropwise at 5° C., 32.7 g (0.33 mol) of methyl cyanoacetate in 50 ml of 1-methyl-2-pyrrolidinone.

The suspension was stirred for 30 mn at 5° C. To the cooled suspension were then rapidly added 70 g (0.3 mol) of 2-bromo-3,5-dichloropyridine and the mixture was heated at 130° C. for 5 hours. After cooling, the reaction mixture was poured into ice water. The aqueous phase was extracted with ethyl ether (3×300 ml) and the organic phase was washed with brine and dried over magnesium sulphate.

The solvent was evaporated under reduced pressure and crude product was recrystallized in methanol to give methyl cyano(3,5-dichloro-2-pyridinyl)acetate: 24.8 g (34%) as brown crystals; m.p.=109-110° C.

Step 2: Preparation of (3,5-dichloro-2-pyridinyl)acetonitrile

To a solution of 14.45 g (0.06 mol) of methyl cyano(3,5-dichloro-2-pyridinyl)acetate in 70 ml of a 25/1 mixture of dimethylsulfoxide/water, was added 1.75 g (0.03 mol) of sodium chloride.

The mixture was stirred for 4 hours at 130° C. After cooling, the reaction mixture was poured into ice water. The aqueous phase was extracted with ethyl ether (3×250 ml) and the organic phase was washed with brine and dried over magnesium sulphate. The solvent was evaporated under reduced pressure to give 11.2 g of the crude product as a brown oil.

The crude product was purified by flash chromatography on silica gel (eluent: heptane/ethyl acetate: 7/3) to give (3,5-dichloro-2-pyridinyl)acetonitrile: 8.65 g (77%) as a yellow oil; mass spectrum: 185 (M−1).

Step 3: Preparation of N-[2-(3,5-dichloro-2-pyridinyl)ethyl]-2-(trifluoromethyl)benzamide (compound 1)

To a solution of 1 g (5.4 mmol) of (3,5-dichloro-2-pyridinyl)acetonitrile in 15 ml of methanol were rapidly added 1.3 g (5.9 mmol) of colbalt(II) chloride hexahydrate and 3.9 g (10.8 mmol) of 2-trifluoromethylbenzoic anhydride.

The dark green solution was cooled to −5° C. and 1.4 g (37.4 mmol) of sodium borohydride was added portion-wise at 0° C.

The reaction mixture was stirred at room temperature for 18 hours. The reaction mixture was neutralized by 1N hydrochloric acid and methanol was remove under reduced pressure. The aqueous phase was reextracted by ethyl acetate and the organic phase was washed with brine and dried over magnesium sulphate. The solvent was evaporated under reduced pressure to give 2.6 g of the crude product as a brown oil.

The crude product was purified by flash chromatography on silica gel (eluent: heptane/ethyl acetate: 7/3) to give N-[2-(3,5-dichloro-2-pyridinyl)ethyl]-2-(trifluoromethyl)benzamide: 0.80 g (41%) as white crystals; m.p.=118° C.

The following compounds of formula (I) are prepared according to a process identical to the one used for the preparation of compound 1, and illustrate as well the present invention: 10, 11, 12 and 15.

Example of Process C/D

Preparation of N-[2-(3-chloro-2-pyridinyl)ethyl]-2-(trifluoromethyl)benzamide (compound 6)

Step 1: Preparation of (3-chloro-2-pyridinyl)acetonitrile

To a solution of 55.5 ml (0.138 mol) of 2.5 M butyl lithium in 400 ml of anhydrous tetrahydrofurane at −78° C., were added 6.22 g (0.153 mol) of acetonitrile. The reaction mixture was stirred 45 mn at −78° C. until formation of a suspension.

To the resulting suspension, a solution of 3 g (0.02 mol) of 2,3-dichloropyridine in 50 ml of anhydrous tetrahydrofurane was slowly added at −78° C. and the reaction mixture was further stirred 2 hours at −78° C.

The reaction mixture was poured into 50 ml of water. The aqueous phase was extracted with dichloromethane and the organic phase was washed with water and dried over magnesium sulphate.

The solvent was evaporated under reduced pressure and the residue was purified by flash chromatography on silica gel (eluent: dichloromethane) to give (3-chloro-2-pyridinyl)acetonitrile as an oil: 1.2 g (40%); mass spectrum: 153 (M+1).

Step 2: Preparation of N-[2-(3-chloro-2-pyridinyl)ethyl]-2-(trifluoromethyl)benzamide (compound 6)

To a solution of 0,152 g (1 mmol) of (3-chloro-2-pyridinyl)acetonitrile in 4 ml of methanol was successively added 0.238 g (1 mmol) of nickel(II) chloride hexahydrate, 0.724 g (2 mmol) of 2-trifluoromethylbenzoic anhydride and slowly added at 0° C., 0.265 g (7 mmol) of sodium borohydride.

The reaction mixture was stirred at room temperature for 18 hours. The solvent was evaporated and the residue was purified by flash chromatography on silica gel (eluent: heptane/ethyl acetate: 9/1) to give N-[2-(3-chloro-2-pyridinyl)ethyl]-2-(trifluoromethyl)benzamide as an oil: 90 mg (27%); mass spectrum: 31.9 (M+1).

The following compounds of formula (I) are prepared according to a process identical to the one used for the preparation of compound 6, and illustrate as well the present invention: 7, 8 and 9.

Example of Process G

Preparation of N-[2-(5-methyl-2-pyridinyl)ethyl]-2-(iodo)benzamide (compound 14)

Step 1: Preparation of 5-methyl-2-vinylpyridine

To a solution of 3 g (17.4 mmol) of 2-bromo-5-methylpyridine in 30 ml of dimethylformamide was successively added 2 g (1.7 mmol) of tetrakis (triphenylphosphine)palladium and 5.52 g (17.4 mmol) of tributyl(vinyl)tin. The reaction mixture was stirred at 120° C. for 18 hours. After cooling, the reaction mixture was poured into 50 ml of water saturated with potassium fluoride and stirred for 1 hour.

The mixture was filtered on supersel and the aqueous phase was extracted with ethyl ether. The organic phase was washed twice with water saturated with potassium fluoride, once with water and dried over magnesium sulphate. The solvent was evaporated under reduced pressure to give 3.5 g of a crude mixture as a yellow oil.

The mixture was purified by flash chromatography on silica gel (eluent: heptane/ethyl acetate: 4/1) to give 5-methyl-2-vinylpyridine as a yellow oil: 0.9 g (43%); mass spectrum: 120 (M+1).

Step 2: Preparation of 2-[2-(5-methyl-2-pyridinyl)ethyl]-1H-isoindole-1,3(2H)-dione 0.5 g (4.2 mmol) of 5-methyl-2-vinylpyridine and 0.618 g (4.2 mmol) of phthalimide was added to 0.5 ml of benzyltrimethylammonium hydroxide (Triton B™) and the mixture was heated at 200° C. for 3 hours.

The mixture was allowed to cool to room temperature and was directly purified by flash chromatography on silica gel (eluent: heptane/ethyl acetate: 5/1) to give 2-[2-(5-methyl-2-pyridinyl)ethyl]-1H-isoindole-1,3(2H)-dione as white crystals: 0.680 g (59%); mass spectrum: 267 (M+1).

Step 3: Preparation of 2-(5-methyl-2-pyridinyl)ethanamine

To a solution of 0.5 g (1.88 mmol) of 2-[2-(5-methyl-2-pyridinyl)ethyl]-1H-isoindole-1,3(2H)-dione in 5 ml of methanol, was added 0.45 g (7.5 mmol) of hydrazine hydrate. The reaction mixture was reflux for 1 hour until completion.

The solvent was removed under vacuum and the residue was acidified with 1 N hydrochloric acid. The solid phthalhydrazide was removed by filtration. The filtrate was basified with sodium hydroxyde and extracted by chloroform. The organic phase was washed with water and dried over magnesium sulphate.

The solvent was evaporated to give pure 2-(5-methyl-2-pyridinyl)ethanamine as a yellow oil: 0.240 g (94%); mass spectrum: 137 (M+1).

Step 4: Preparation of N-[2-(5-methyl-2-pyridinyl)ethyl]-2-(iodo)benzamide (compound 14)

To 0.06 mg (0.44 mmol) of 2-(5-methyl-2-pyridinyl)ethanamine in solution in 3 ml of acetonitrile, was successfully added 0.117 mg (0.44 mmol) of 2-iodobenzoyl chloride and 0.078 mg (0.44 mmol) of potassium carbonate.

The reaction mixture was stirred at room temperature for 18 hours. The reaction mixture was poured into aqueous potassiumcarbonate and the aqueous phase was extracted with ethyl acetate. The organic phase was washed with brine and dried over magnesium sulphate.

The solvent was evaporated under reduced pressure to give pure N-[2-(5-methyl-2-pyridinyl)ethyl]-2-(iodo)benzamide as beige crystals: 0.08 g (53%); mass spectrum: 367 (M+1).

The compounds 18, 19, 20 and 24 are prepared according to a process identical to the one used for the preparation of compound 14, and illustrate as well the present invention.

EXAMPLES OF BIOLOGICAL ACTIVITY OF THE COMPOUND OF GENERAL FORMULA (I)

Example A

In Vivo Test on *Alternaria brassicae* (Leaf Spot of Crucifers)

The active ingredient tested is prepared by potter homogenisation in a concentrated suspension type formulation at 100 g/l. This suspension is then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per $cm^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) or total protection is observed at a dose of 330 ppm with the following compounds: 1, 2, 3, 4, 5, 6, 7, 8, 9, 10, 11, 12, 13, 14, 15, 16, 17, 18, 19, 20, 21, 24, 25, 26, 27, 28, 30, 31, 32, 34, 35, 36, 37, 38, 40, 41, 43, 45, 47, 49, 50, 51, 52, 53, 54, 55, 56, 57, 58, 59, 60, 61, 62, 63, 67 and 68.

Example B

In Vivo Test on *Erysiphe graminis* f. sp. *tritici* (Powdery Mildew of Wheat)

The active ingredient tested is prepared by potter homogenisation in a concentrated suspension type formulation at 100 g/l. This suspension is then diluted with water to obtain the desired active material concentration.

Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

Under these conditions, good (at least 50%) or total protection is observed at a dose of 330 ppm with the following compounds: 1, 3, 4, 5, 6, 8, 9, 10, 11, 12, 13, 18, 38, 50, 43 and 45.

Example C

In Vivo Test on *Botrytis cinerea* (Cucumber Grey Mould)

The active ingredient tested is prepared by potter homogenisation in a concentrated suspension type formulation at 100 g/l. This suspension is then diluted with water to obtain the desired active material concentration.

Cucumber plants (Marketer variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatin
50 g/L of cane sugar
2 g/L of NH4NO3
1 g/L of KH2PO4

The contaminated cucumber plants are settled for 5/7 days in a climatic room at 15-11° C. (day/night) and at 80% relative humidity.

Grading is carried out 5/7 days after the contamination, in comparison with the control plants. Under these conditions, good (at least 50%) or total protection is observed at a dose of 330 ppm with the following compounds: 1, 2, 3, 4, 5, 6, 9, 10, 13, 18, 21, 22, 23, 25, 26, 27, 28, 29, 32, 34, 35, 38, 40, 43, 44, 45, 46, 47, 50, 51, 52, 53, 57 and 62.

Example D

In Vivo Test on *Pyrenophora teres* (Barley Net Blotch)

The active ingredient tested is prepared by potter homogenisation in a concentrated suspension type formulation at 100 g/l. This suspension is then diluted with water to obtain the desired active material concentration.

Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 50%) or total protection is observed at a dose of 330 ppm with the following compounds: 1, 2, 3, 4, 5, 9, 10, 11, 12, 13, 16, 18, 19, 21, 28, 34, 35, 36, 37, 38, 39, 40, 41, 42, 43, 45, 47, 48, 49, 50, 51, 52, 53, 54, 55, 56, 57, 58, 59, 60, 61, 62, 63, 65, 67, and 68.

The N-{1-methylcarbamoyl-2-[3-chloro-5-(trifluoromethyl)-2-pyridinyl]-ethyl}-4-phenylbenzamide disclosed by Patent Application WO 01/11965 (see compound 316 in Table D) showed poor effectiveness on *Alternaria brassicae*, and zero effectiveness on *Botrytis cinerea* at 330 ppm; the N-{1-ethylcarbamoyl-2-[3-chloro-5-(trifluoromethyl)-2-pyridinyl]ethyl}-3-nitrobenzamide also disclosed by Patent Application WO 01/11965 (see compound 307 in Table D) showed poor effectiveness on *Alternaria brassicae* and zero effectiveness on *Botrytis cinerea* at 330 ppm; the N-{1-ethylcarbamoyl-2-[3-chloro-5-(trifluoromethyl)-2-pyridinyl]-ethyl}-benzamide and the N-{1-methylcarbamoyl-2-[3-chloro-5-(trifluoromethyl)-2-pyridinyl]ethyl}-benzamide also disclosed by Patent Application WO 01/11965 (see compounds 304 and 314 in Table D) showed zero effectiveness on *Botrytis cinerea* at 330 ppm; and the N-{1-ethylcarbamoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-2-bromobenzamide and the N-{1-methylcarbamoyl-2-[3-chloro-5-(trifluoromethyl)-2-pyridinyl]ethyl}-4-methoxybenzamide also disclosed by Patent Application WO 01/11965 (see compounds 306, 310 and 315 in Table D) showed zero effectiveness on *Botrytis cinerea* at 330 ppm.

The invention claimed is:

1. A compound of formula (I):

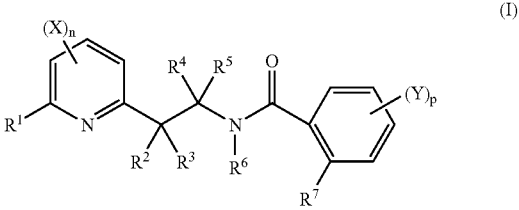

in which:

n is 1, 2 or 3;

each X is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

$R^1$ is selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl optionally substituted with 1 to 5 halogen atoms, a benzylamino, a phenoxy, a phenylsulfanyl optionally substituted with 1 to 5 halogen atoms and a phenylamino;

with the proviso that X and $R^1$ are not both a hydrogen atom;

$R^2$ and $R^3$ are independently selected from the group consisting of a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonyloxy and a $C_1$-$C_6$-alkylcarbonylamino;

or $R^2$ and $R^3$ may together form a 3-, 4-, 5- or 6-membered carbocycle;

$R^4$ and $R^5$ are independently selected from the group consisting of a hydrogen atom, a halogen atom, a cyano group, a $C_1$-$C_6$-alkyl and a $C_1$-$C_6$-halogenoalkyl having 1 to 5 halogen atoms;

or $R^4$ and $R^5$ may together form a 3-, 4-, 5- or 6-membered carbocycle;

$R^6$ is selected from the group consisting of a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-cycloalkyl, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl and a $C_1$-$C_6$-halogenoalkylsulfonyl having 1 to 5 halogen atoms;

p is 1, 2, 3 or 4;

each Y is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms and a $C_1$-$C_8$-alkylsulfonamide; and $R^7$ is selected from the group consisting of a halogen atom, a nitro group, a cyano group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms and a $C_1$-$C_8$-alkylsulfonamide;

as well as a salt or N-oxide thereof.

2. The compound of claim 1 wherein $R^1$ is a hydrogen atom or a halogen atom.

3. The compound of claim 1 wherein n is 1 or 2.

4. The compound of claim 1 wherein each X is selected from the group consisting of a halogen atom and a $C_1$-$C_8$-alkyl.

5. The compound of claim 1 wherein the 2-pyridyl is substituted by X in the 3- and/or in the 5-position.

6. The compound of claim 1 wherein $R^7$ is selected from the group consisting of a halogen atom, a $C_1$-$C_8$-alkyl and a $C_1$-$C_8$-halogenoalkyl having 1 to 5 halogen atoms.

7. The compound of claim 1 wherein p is 1 or 2.

8. The compound of claim 7 wherein p is 1.

9. The compound of claim 1 wherein each Y is selected from the group consisting of a hydrogen atom, a halogen atom and a $C_1$-$C_8$-alkyl.

10. The compound of claim 9 wherein each Y is a hydrogen atom.

11. The compound of claim 1 wherein the phenyl is substituted by Y first in the para position.

12. A process for the preparation of a compound of formula (Ia)

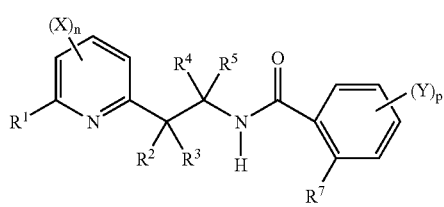

wherein:

$R^1$, $R^7$, X, Y, n and p are as defined in claim 1;
$R^2$, $R^4$, and $R^5$ are hydrogen atoms;
$R^3$ is a $C_1$-$C_6$ alkyl;

which process comprises:

a first step according to reaction scheme A-1:

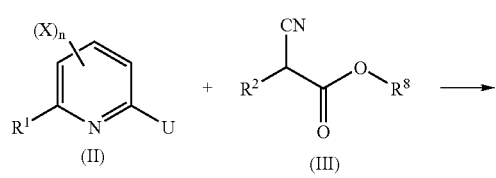

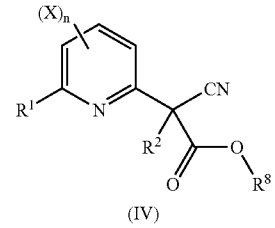

in which:

$R^8$ is selected from the group consisting of a $C_1$-$C_6$ alkyl, a $C_1$-$C_6$ haloalkyl, a benzyl, 4-methoxybenzyl and pentafluorophenyl;

U is a leaving group selected from the group consisting of a halogen, a $C_1$-$C_6$ alkylsulfonate and a $C_1$-$C_6$ haloalkylsulfonate;

comprising the arylation of a cyanoacetate derivative of formula (III) by a pyridine derivative of formula (II), to provide a 2-(pyridyl)cyanoacetate derivative of formula (IV), in the presence of a base, at a temperature of from 0° C. to 200° C.;

a second step according to reaction scheme A-2:

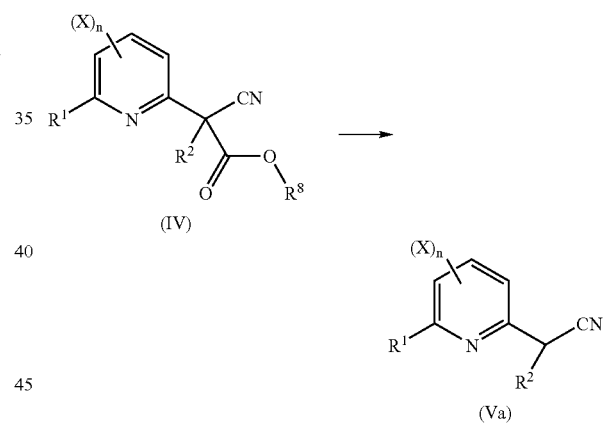

in which:

comprising a basic hydrolysis, an acidic hydrolysis or a displacement by a halide of a compound of formula (IV) to provide, upon heating at a temperature of from 40° C. to reflux, a 2-pyridylacetonitrile derivative of formula (Va);

a third step according to reaction scheme A-3:

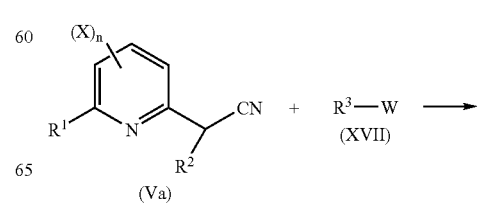

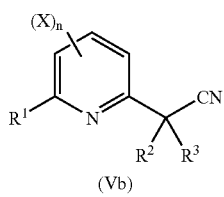

(Vb)

in which:
W is selected from the group consisting of a halogen atom, a $C_1$-$C_6$ alkylsulfonate, a $C_1$-$C_6$ haloalkylsulfonate and a 4-methyl-phenylsulfonate, comprising the alkylation of a compound of formula (Va) by a reagent of formula (XVII) to provide a compound of formula (Vb);

a fourth step according to reaction scheme A-4:

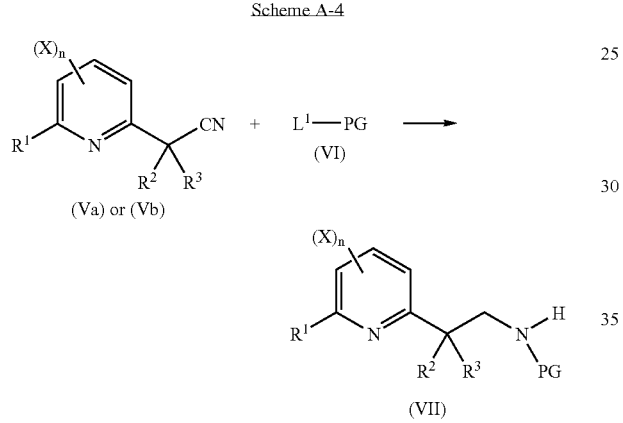

in which:
L$^1$ is a leaving group selected from the group consisting of an —OR$^8$ group and an —OCOR$^8$ group,
PG represents a protecting group selected from the group consisting of a —COOR$^8$ group and a —COR$^8$ group, comprising the reduction, by hydrogenation or by an hydride donor, of a compound of formula (Vb), in the presence of a catalyst and in the presence of a compound of formula (VI) to produce a compound of formula (VII), at a temperature of from 0° C. to 150° C. and under a pressure of from 1 bar and 100 bar;

a fifth step according to reaction scheme A-5:

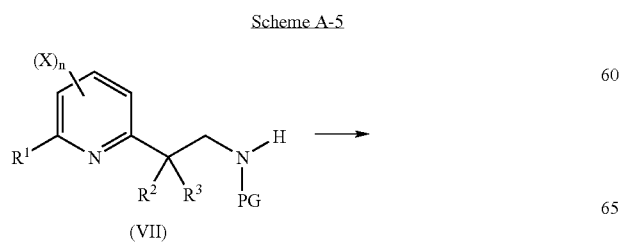

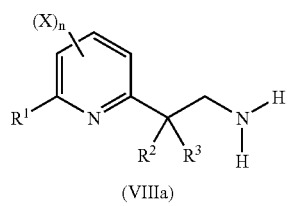

(VIIIa)

comprising a deprotection reaction, in an acidic or in a basic medium, of a compound of formula (VII) to provide an amine derivative of formula (VIIIa) or one of its salts; and a sixth step according to reaction scheme A-6:

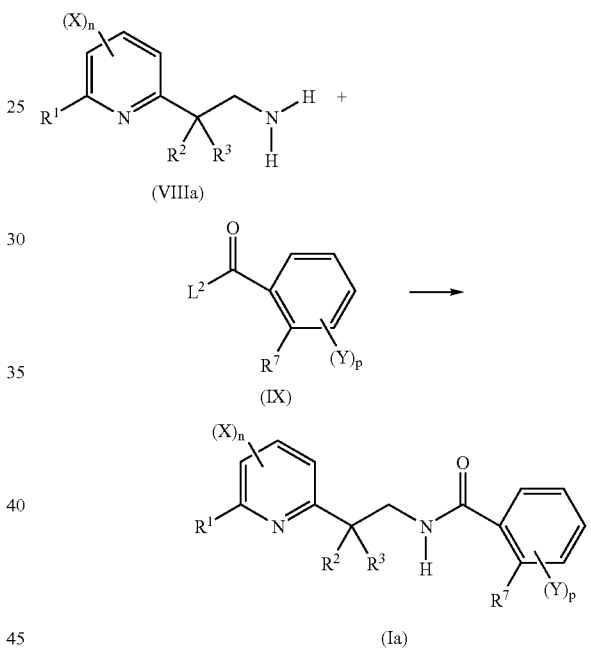

in which:
L$^2$ is a leaving group selected from the group consisting of a halogen atom, a hydroxyl group, an OR$^8$ group, an OCOR$^8$,
and a group of formula

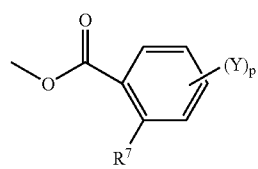

comprising a coupling reaction of an amine derivative of formula (VIIIa) or one of its salts, with a carboxylic acid derivative of formula (IX) to provide a compound of formula (Ia).

13. The process of claim 12 further comprising a step according to reaction scheme G:

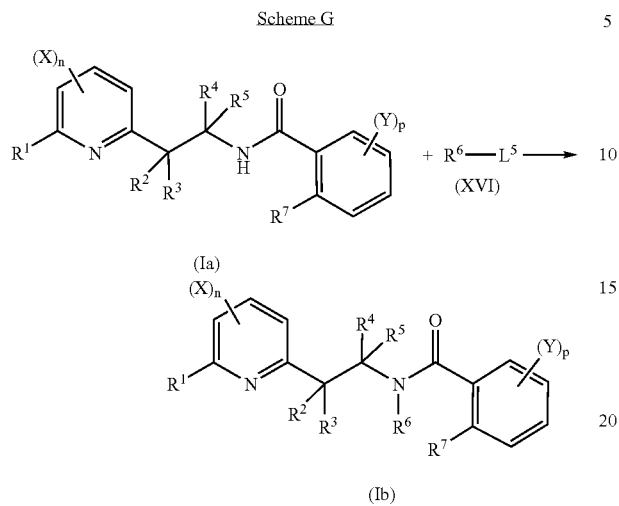

in which:

R⁶ is a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-cycloalkyl, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalkylsulfonyl having 1 to 5 halogen atoms; and $L^5$ is a leaving group selected from the group consisting of a halogen atom, a 4-methyl phenylsulfonyloxy, and a methylsulfonyloxy;

comprising the reaction of a compound of formula (Ia) with a compound of formula (XVI) to provide a compound of formula (Ib).

14. Fungicidal composition comprising an effective amount of a compound according to claim 1 and an agriculturally acceptable support.

15. Method for treating phytopathogenic fungi of crops comprising applying an effective and non-phytotoxic amount of a composition according to claim 14 to the plant seeds or to the plant leaves and/or to the fruits of the plants or to the soil in which the plants are growing or in which it is desired to grow them.

* * * * *